(12) United States Patent
Saijo et al.

(10) Patent No.: US 11,691,980 B2
(45) Date of Patent: Jul. 4, 2023

(54) LIPHAGAL ANALOG AND MULTI-TARGETED KINASE INHIBITOR CONTAINING LIPHAGAL OR ANALOG THEREOF

(71) Applicant: TOHOKU UNIVERSITY, Miyagi (JP)

(72) Inventors: Ken Saijo, Miyagi (JP); Chikashi Ishioka, Miyagi (JP); Tadashi Katoh, Miyagi (JP); Koichi Narita, Miyagi (JP)

(73) Assignee: TOHOKU UNIVERSITY, Miyagi (JP)

(*) Notice: Subject to any disclaimer, the term of this patent is extended or adjusted under 35 U.S.C. 154(b) by 308 days.

(21) Appl. No.: 16/610,165

(22) PCT Filed: May 1, 2018

(86) PCT No.: PCT/JP2018/017470
§ 371 (c)(1),
(2) Date: Nov. 1, 2019

(87) PCT Pub. No.: WO2018/203564
PCT Pub. Date: Nov. 8, 2018

(65) Prior Publication Data
US 2021/0198271 A1    Jul. 1, 2021

(30) Foreign Application Priority Data

May 2, 2017 (JP) .................................. 2017-091712

(51) Int. Cl.
| C07D 409/04 | (2006.01) |
| C07D 307/93 | (2006.01) |
| C07D 317/64 | (2006.01) |
| C07C 47/57  | (2006.01) |
| C07D 307/94 | (2006.01) |
| C07D 493/04 | (2006.01) |

(52) U.S. Cl.
CPC ............ *C07D 493/04* (2013.01); *C07C 47/57* (2013.01); *C07D 307/93* (2013.01); *C07D 307/94* (2013.01); *C07D 317/64* (2013.01)

(58) Field of Classification Search
None
See application file for complete search history.

(56) References Cited

FOREIGN PATENT DOCUMENTS

| ES | 2 127 690    | 4/1999  |
| JP | 2007-204380  | 8/2007  |
| JP | 2015-514701  | 5/2015  |
| JP | 2016-529250  | 9/2016  |
| WO | 95/06626     | 3/1995  |
| WO | 2005/117869  | 12/2005 |
| WO | 2006/081659  | 8/2006  |
| WO | 2012/166987  | 12/2012 |
| WO | 2013/140417  | 9/2013  |
| WO | 2015/019121  | 2/2015  |

OTHER PUBLICATIONS

Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Tetsu et al., Proliferation of cancer cells despite CDK2 inhibition. Cancer Cells, 2003, 3, 233-245.*
Dethe et al., "Enantiospecific total syntheses of meroterpenoids (−)-F1839-I and (−)-corallidictyals B and D", Organic & Biomolecular Chemistry, 2017, vol. 15, pp. 65-68.
Chan et al., Protein Kinase C. Inhibitors: Novel Spirosesquiterpene Aldehydes From a Marine Sponge *Aka (=Siphonodictyon) Coralliphagun*, Journal of Natural Products, Nov. 1994, vol. 57, No. 11, pp. 1543-1548.
Kikuchi et al., "Enantioselective Total Synthesis of (−)-Siphonodictyal B and (+)-8-epi-Siphonodictyal B with Phosphatidylinositol 3-Kinase α (PI3Kα) Inhibitory Activity", Eur. J. Org. Chem., 2016, pp. 5659-5666.
Brylinski et al., "Comprehensive Structural and Functional Characterization of the Human Kinome by Protein Structure Modeling and Ligand Virtual Screening", J. Chem. Inf. Model., 2010, vol. 50, No. 10, pp. 1839-1854.
Pereira et al., "Synthesis of Phosphatidylinositol 3-Kinase (PI3K) Inhibitory Analogues of the Sponge Meroterpenoid Liphagai", J. Med. Chem., 2010, vol. 53, No. 24, pp. 8523-8533.
Chikamatsu et al., "Identification and characterization of terpenoid analogues as multi-target kinase inhibitors", Cancer Science, Jan. 2018, vol. 109, supplement 1, abstract No. P-2349.
Marion et al., "Liphagai, a Selective Inhibitor of PI3 Kinase α Isolated from the Sponge *Aka coralliphaga*: Structure Elucidation and Biomimetic Synthesis", Organic Letters, 2006, vol. 8, No. 2, pp. 321-324.

(Continued)

*Primary Examiner* — Po-Chih Chen
(74) *Attorney, Agent, or Firm* — Wenderoth, Lind & Ponack, L.L.P.

(57) ABSTRACT

A method of treating a disease that is treatable through inhibition of at least one kinase selected from the group consisting of CDK7, CDK4, CDK6, PIM2, TSSK3, MST4, NEK6, MAP3K, MST3, DDR1, SPHK1, CaMK1, AurA, BRK, CaMK4, and PIM1, the method comprising administering an effective dose of a compound represented by the following formula (1) or a salt thereof to a patient:

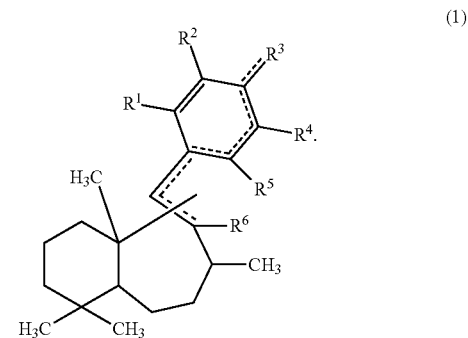

(1)

2 Claims, 11 Drawing Sheets

(56) References Cited

OTHER PUBLICATIONS

Kamishima et al., "Biogenetically Inspired Total Synthesis of (+)-Liphagal: A Potent and Selective Phosphoinositide 3-Kinase $\alpha$ (PI3K$\alpha$) Inhibitor from the Marine Sponge *Aka coralliphaga*", Eur. J. Org. Chem., 2014, pp. 3443-3450.
International Search Report dated Jul. 10, 2018 in International (PCT) Application No. PCT/JP2018/017470.
Extended European Search Report dated Jan. 12, 2021 in European Patent Application No. 18794860.9.

* cited by examiner

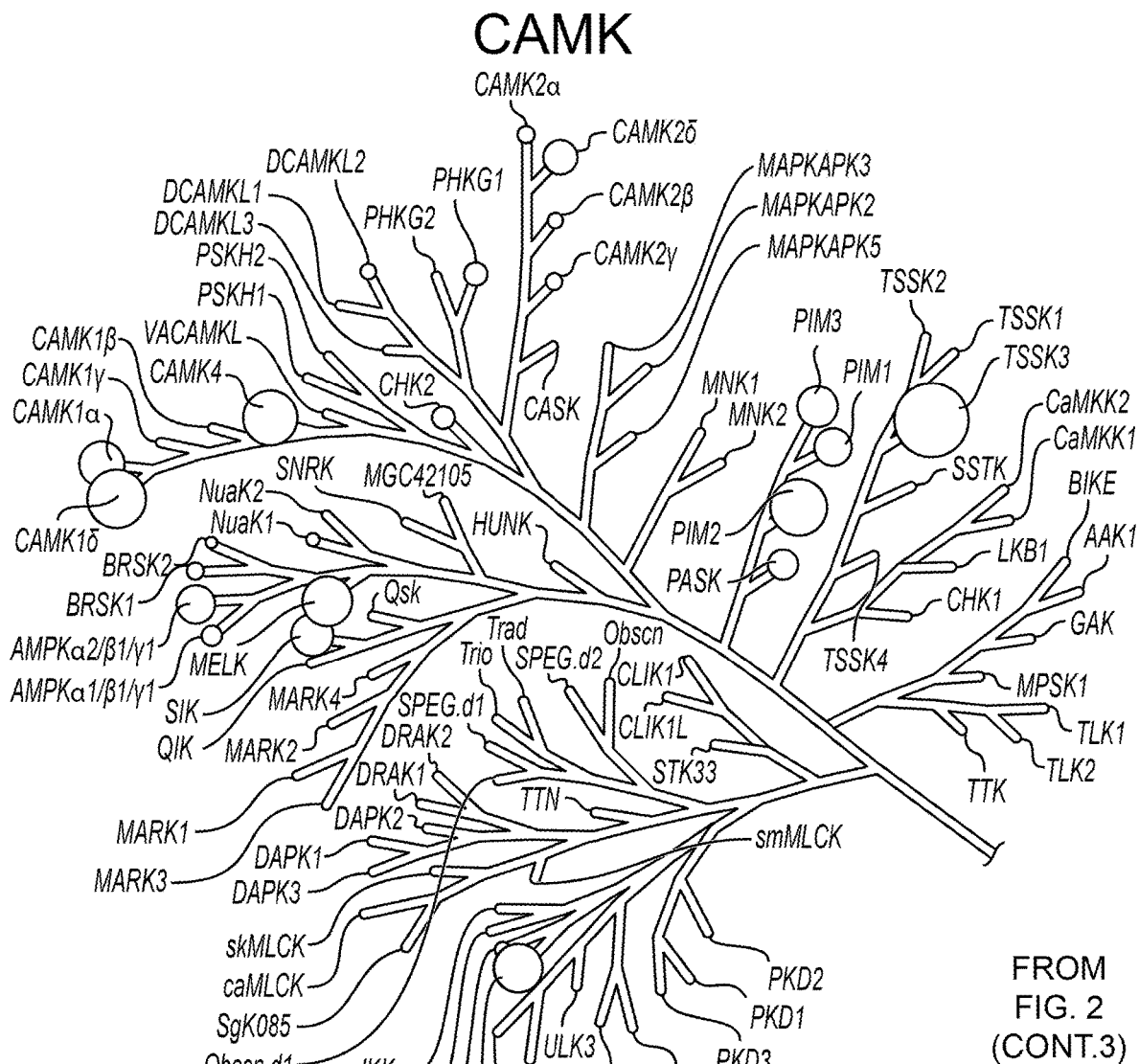
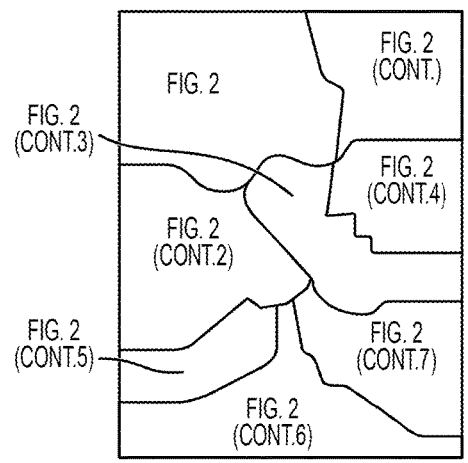
FIG. 2 (CONT.2)

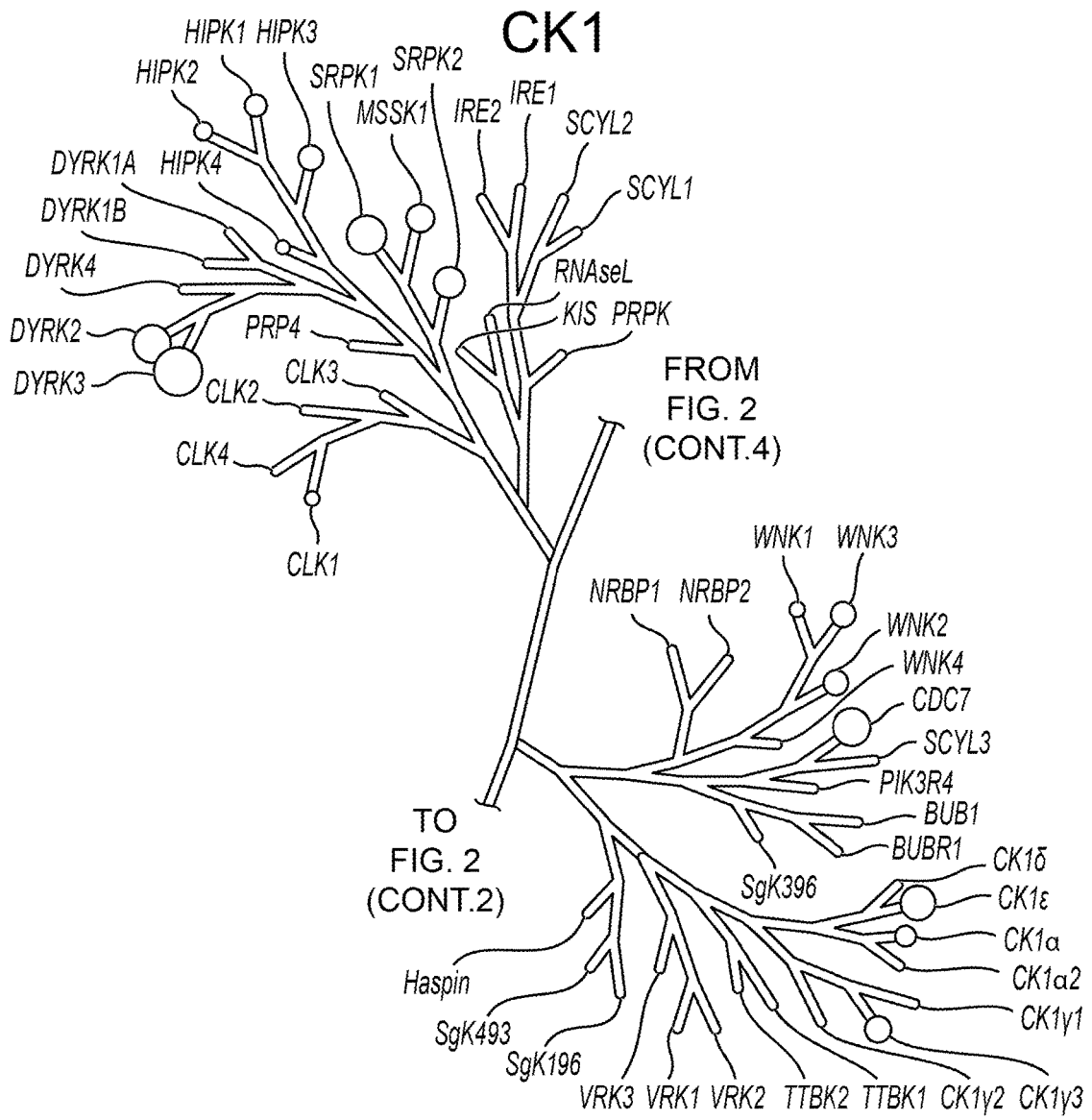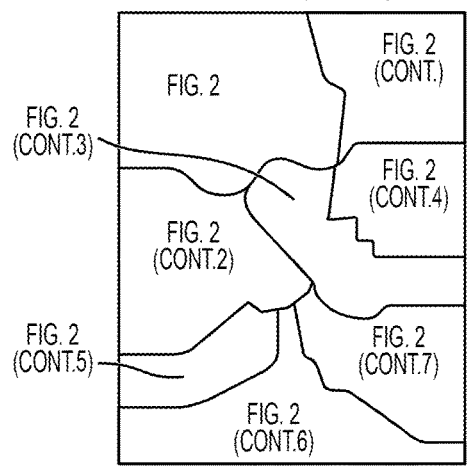
FIG. 2 (CONT.3)

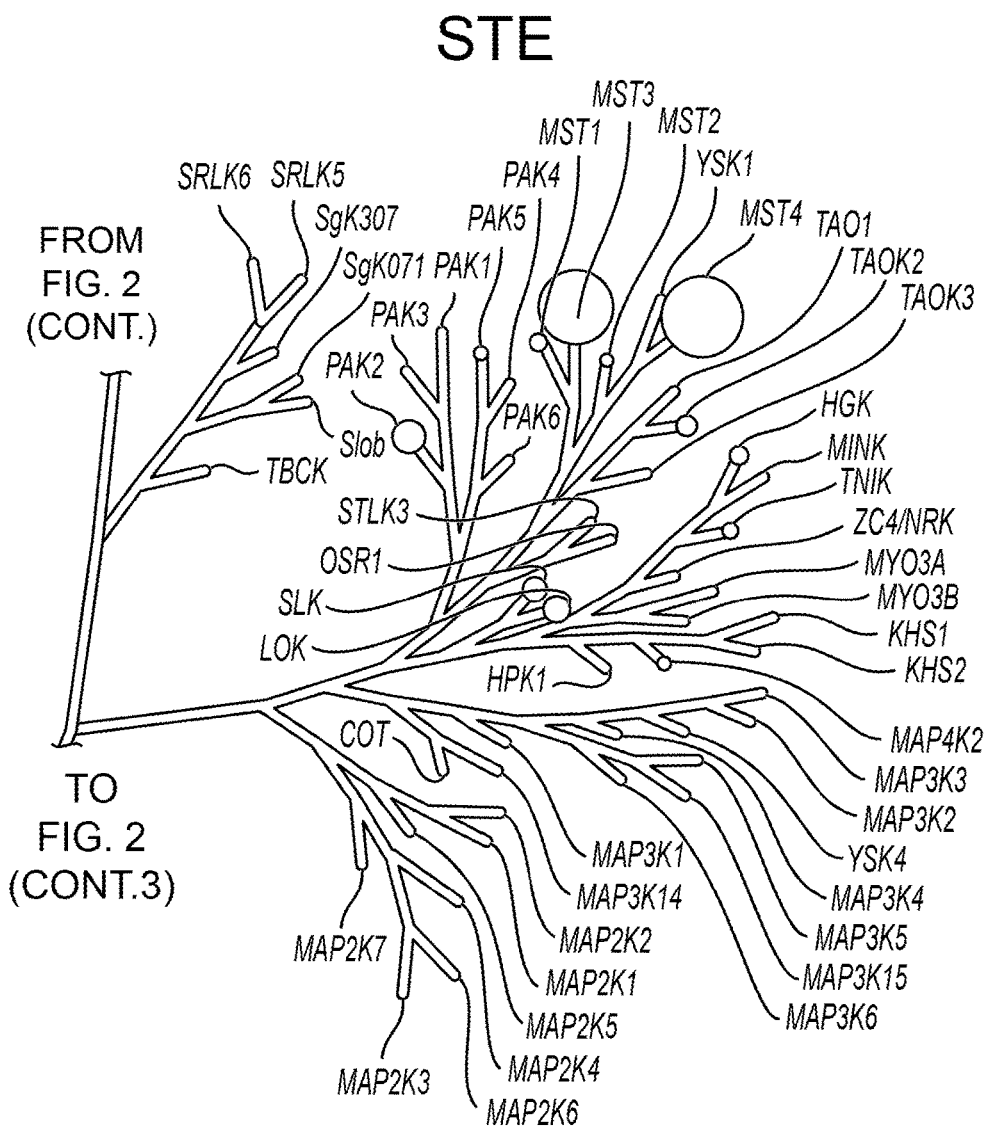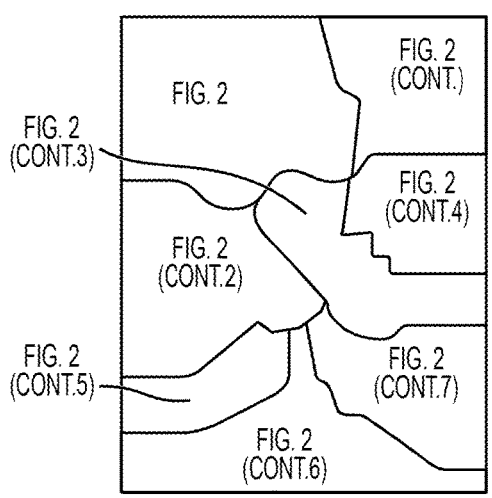
FIG. 2 (CONT.4)

OTHER

*(CONT.5)*

*(CONT.6)*

(CONT.7)

LIPHAGAL ANALOG AND MULTI-TARGETED KINASE INHIBITOR CONTAINING LIPHAGAL OR ANALOG THEREOF

TECHNICAL FIELD

The present invention relates to a liphagal analog and a multi-targeted kinase inhibitor containing liphagal or an analog thereof.

BACKGROUND ART

Molecularly targeted therapeutic agents, each of which targets a certain molecule (typically a factor activated in a certain disease) to control a function thereof, can be expected to suppress side effects while providing therapeutic effects. Accordingly, research and development thereof have been promoted in the field of treatment of diseases, such as cancer. In addition, a large number of molecularly targeted therapeutic agents are commercially available.

Meanwhile, however, a mechanism of proliferation of cancer cells is complicated, and hence a sufficient therapeutic effect may not be obtained even when a function of one molecule is suppressed. Accordingly, a molecularly targeted drug having a plurality of target molecules is effective in some cases. In fact, a plurality of multi-targeted molecularly targeted drugs have been used in clinical settings. However, there is a strong demand for further development of multi-targeted molecularly targeted drugs.

CITATION LIST

Patent Literature

PTL 1: WO 2006/081659 A1
PTL 2: JP 2015-514701 A

Non-Patent Literature

NPL 1: Org. Lett. Vol. 8, No. 2, 2006 p 321-324
NPL 2: J. Med. Chem. 2010, 53, 8523-8533
NPL 3: Eur. J. Org. Chem. 2014, 3443-3450

SUMMARY OF INVENTION

Technical Problem

The present invention is directed to the provision of an inhibitor for a kinase other than phosphatidylinositol 3-kinase (PI3K) containing as an active ingredient a compound that has not been known for inhibitory activity against the kinase heretofore.

Solution to Problem

Under such circumstances, the inventors of the present invention have made extensive investigations, and as a result, have found that liphagal inhibits the activities of many kinds of kinases. The inventors of the present invention have also found that various analogs, such as production intermediates, of liphagal, also have inhibitory activity against many kinds of kinases. The present invention is based on such novel findings.

Therefore, the present invention provides an inhibitor, a compound or a salt thereof, and a method that are described in the following items:

Item 1. An inhibitor for at least one kind of kinase selected from the group consisting of CDK7, CDK4, CDK6, PIM2, TSSK3, MST4, NEK6, MAP3K, MST3, DDR1, SPHK1, CaMK1, AurA, BRK, CaMK4, and PIM1, the inhibitor including as an active ingredient a compound represented by the following general formula (1) or a salt thereof:

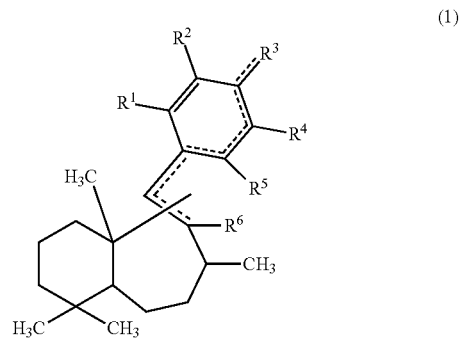

(1)

in the general formula (1), $R^1$, $R^2$, $R^4$, and $R^5$ are identical to or different from each other, and each represent hydrogen, a hydroxy group, an acyl group, a hydroxyalkyl group, or a carboxyl group, $R^3$ represents hydrogen, a hydroxy group, an acyl group, a hydroxyalkyl group, a carboxyl group, or an oxo group (=O), $R^5$ and $R^6$ may together form an oxo group (=O), ------- represents a single bond or a double bond, and a moiety represented by the following general formula A represents the following A-1, A-2, or A-3:

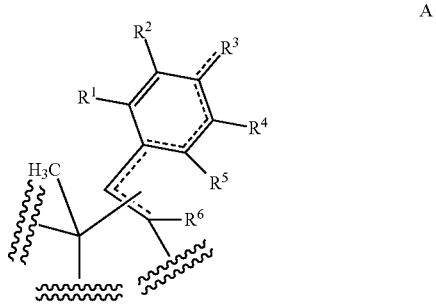

A in the general formula A, $R^1$, $R^2$, $R^3$, $R^4$, $R^5$, and $R^6$ are the same as described above;

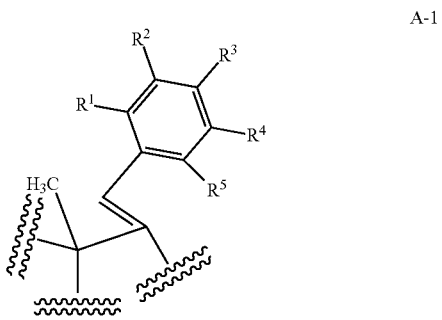

A-1 in the general formula A-1, $R^1$, $R^2$, $R^4$, and $R^5$ are the same as described above, and $R^3$ represents hydrogen, a hydroxy group, an acyl group, a hydroxyalkyl group, or a carboxyl group;

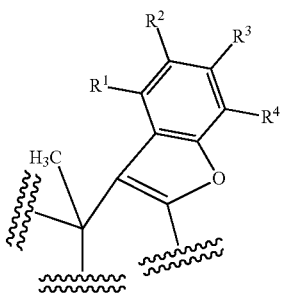

(A-2)

in the general formula A-2, $R^1$, $R^2$, and $R^4$ are the same as described above, and $R^3$ represents hydrogen, a hydroxy group, an acyl group, a hydroxyalkyl group, or a carboxyl group;

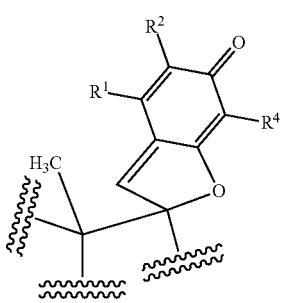

(A-3)

in the general formula A-3, $R^1$, $R^2$, and $R^4$ are the same as described above.

Item 2. The inhibitor according to Item 1, wherein the inhibitor is an inhibitor for: at least one kind of kinase selected from the group consisting of CDK7, CDK4, CDK6, PIM2, TSSK3, MST4, NEK6, MAP3K, MST3, DDR1, SPHK1, CaMK1, AurA, BRK, CaMK4, and PIM1; and PI3K.

Item 3. The inhibitor according to Item 1 or 2, including a compound represented by the following general formula (1-1) or a salt thereof:

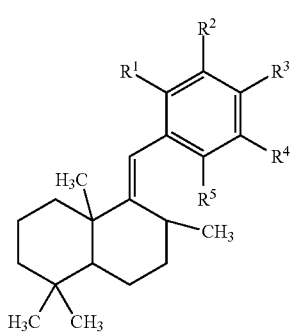

(1-1)

in the general formula 1-1, $R^1$, $R^2$, $R^3$, $R^4$, and $R^5$ are identical to or different from each other, and each represent hydrogen, a hydroxy group, an acyl group, a hydroxyalkyl group, or a carboxyl group.

Item 4. A phosphatidylinositol 3-kinase (PI3K) inhibitor including a compound represented by the following general formula (1-1) or a salt thereof:

(1-1)

in the general formula 1-1, $R^1$, $R^2$, $R^3$, $R^4$, and $R^5$ are identical to or different from each other, and each represent hydrogen, a hydroxy group, an acyl group, a hydroxyalkyl group, or a carboxyl group.

Item 5. A compound represented by the following general formula (1) or a salt thereof:

(1)

in the general formula (1), $R^1$, $R^2$, $R^4$, and $R^5$ are identical to or different from each other, and each represent hydrogen, a hydroxy group, an acyl group, a hydroxyalkyl group, or a carboxyl group, $R^3$ represents hydrogen, a hydroxy group, an acyl group, a hydroxyalkyl group, a carboxyl group, or an oxo group (=O), $R^5$ and $R^6$ may together form an oxo group (=O), represents a single bond or a double bond, and a moiety represented by the following general formula A represents the following A-1, A-2, or A-3:

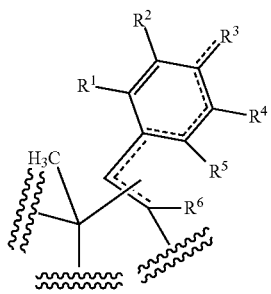

A in the general formula A, $R^1$, $R^2$, $R^3$, $R^4$, $R^5$, and $R^6$ are the same as described above;

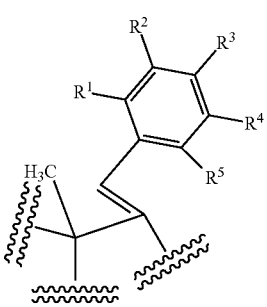

A-1 in the general formula A-1, $R^1$, $R^2$, $R^4$, and $R^5$ are the same as described above, and $R^3$ represents hydrogen, a hydroxy group, an acyl group, a hydroxyalkyl group, or a carboxyl group;

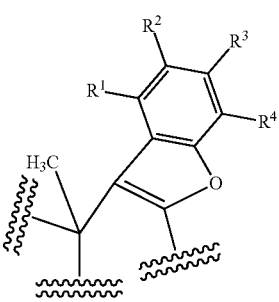

A-2 in the general formula A-2, $R^1$, $R^2$, and $R^4$ are the same as described above, and $R^3$ represents hydrogen, a hydroxy group, an acyl group, a hydroxyalkyl group, or a carboxyl group;

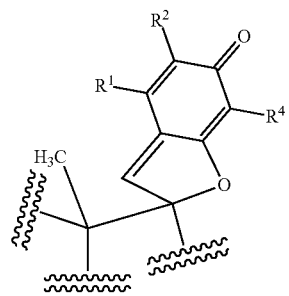

A-3 in the general formula A-3, $R^1$, $R^2$, and $R^4$ are the same as described above, provided that a compound represented by

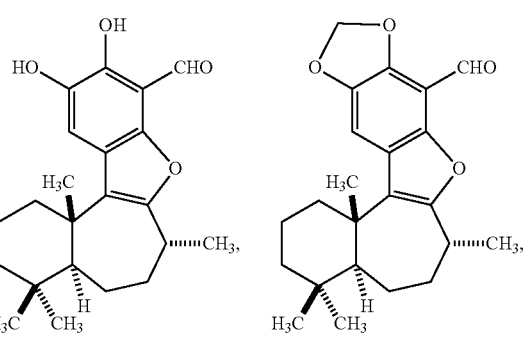

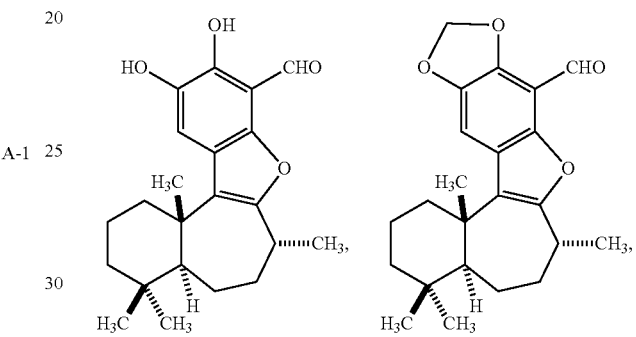

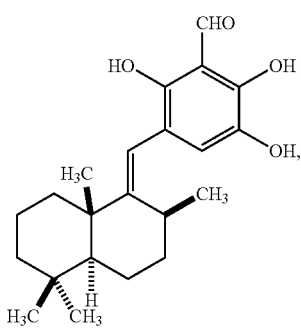

7
-continued

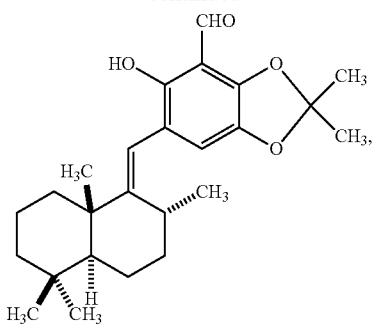

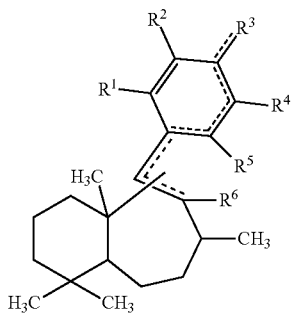

8
-continued

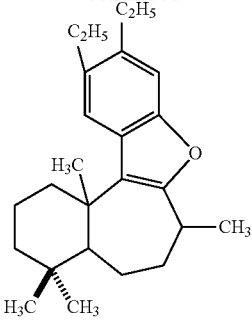

or a salt thereof is excluded.

Item 6. A method of preventing or treating a disease that is treatable through inhibition of at least one kind of kinase selected from the group consisting of CDK7, CDK4, CDK6, PIM2, TSSK3, MST4, NEK6, MAP3K, MST3, DDR1, SPHK1, CaMK1, AurA, BRK, CaMK4, and PIM1, the method including administering an effective dose of a compound represented by the following general formula (1) or a salt thereof to a patient:

(1)

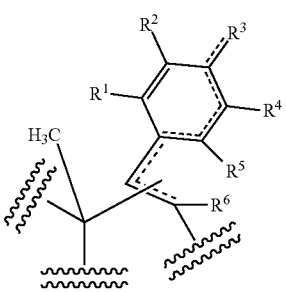

in the general formula (1), $R^1$, $R^2$, $R^4$, and $R^5$ are identical to or different from each other, and each represent hydrogen, a hydroxy group, an acyl group, a hydroxyalkyl group, or a carboxyl group, $R^3$ represents hydrogen, a hydroxy group, an acyl group, a hydroxyalkyl group, a carboxyl group, or an oxo group (═O), $R^5$ and $R^6$ may together foam an oxo group (═O), represents a single bond or a double bond, and a moiety represented by the following general formula A represents the following A-1, A-2, or A-3:

A in the general formula A, $R^1$, $R^2$, $R^3$, $R^4$, $R^5$, and $R^6$ are the same as described above;

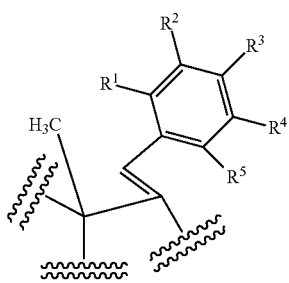

in the general formula A-1, $R^1$, $R^2$, $R^4$, and $R^5$ are the same as described above, and $R^3$ represents hydrogen, a hydroxy group, an acyl group, a hydroxyalkyl group, or a carboxyl group;

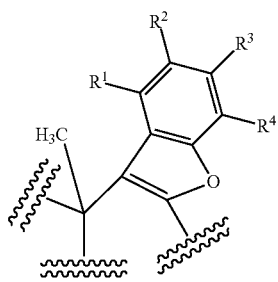

in the general formula A-2, $R^1$, $R^2$, $R^3$, and $R^4$ are the same as described above, and $R^3$ represents hydrogen, a hydroxy group, an acyl group, a hydroxyalkyl group, or a carboxyl group;

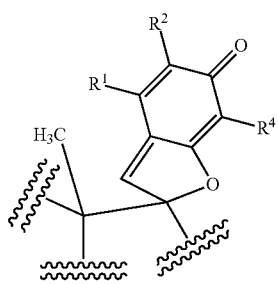

in the general formula A-3, $R^1$, $R^2$, and $R^4$ are the same as described above.

Advantageous Effects of Invention

According to the present invention, the inhibitor for a kinase other than phosphatidylinositol 3-kinase (PI3K) containing as an active ingredient a compound that has not been known for inhibitory activity against the kinase heretofore can be provided.

DESCRIPTION OF EMBODIMENTS

Figure 1:
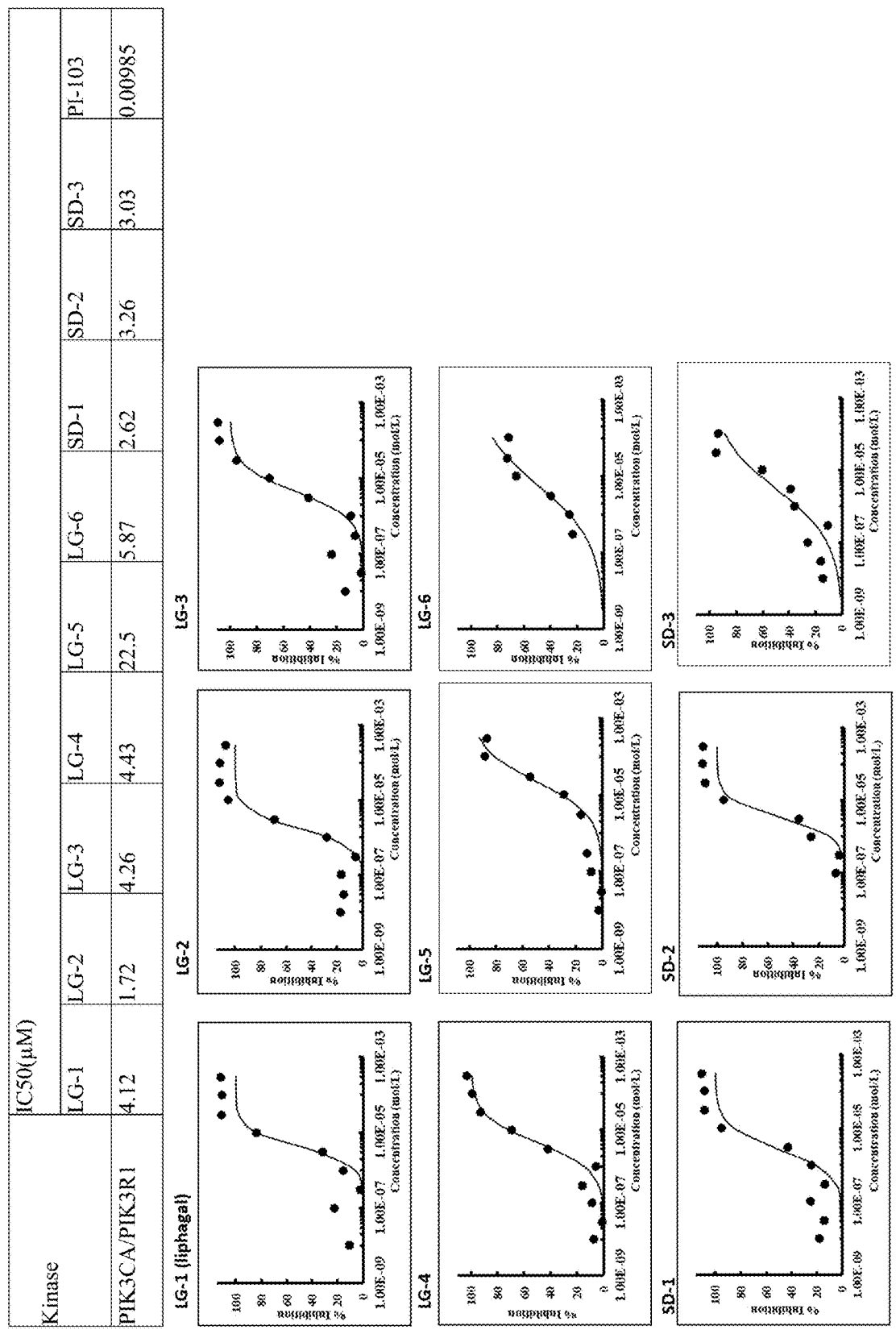
FIG. 1 are graphs for showing the results of assessment of PI3Kα inhibitory activity in Example 1.

The present invention provides an inhibitor for at least one kind of kinase selected from the group consisting of CDK7, CDK4, CDK6, PIM2, TSSK3, MST4, NEK6, MAP3K, MST3, DDR1, SPHK1, CaMK1, AurA, BRK, CaMK4, and PIM1, the inhibitor including as an active ingredient a compound represented by the following general formula (1) or a salt thereof:

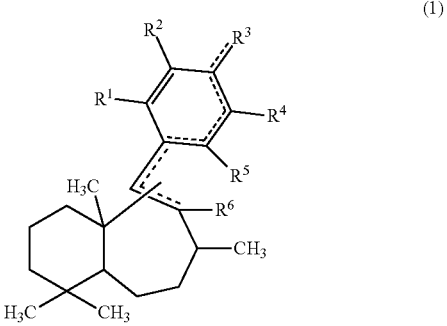

in the general formula (1), $R^1$, $R^2$, $R^4$, and $R^5$ are identical to or different from each other, and each represent hydrogen, a hydroxy group, an acyl group, a hydroxyalkyl group, or a carboxyl group, $R^3$ represents hydrogen, a hydroxy group, an acyl group, a hydroxyalkyl group, a carboxyl group, or an oxo group ($=$O), $R^5$ and $R^6$ may together form an oxo group ($=$O), represents a single bond or a double bond, and a moiety represented by the following general formula A represents the following A-1, A-2, or A-3:

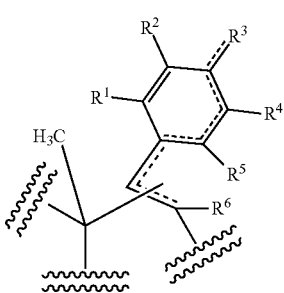

in the general formula A, $R^1$, $R^2$, $R^3$, $R^4$, $R^5$, and $R^6$ are the same as described above;

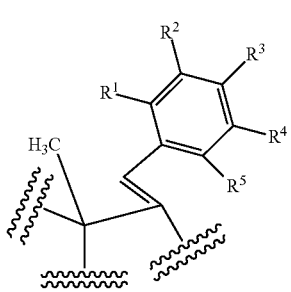

A-1 in the general formula A-1, $R^1$, $R^2$, $R^4$, and $R^5$ are the same as described above, and $R^3$ represents hydrogen, a hydroxy group, an acyl group, a hydroxyalkyl group, or a carboxyl group;

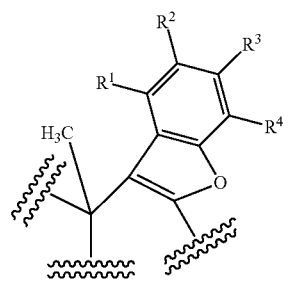

A-2 in the general formula A-2, $R^1$, $R^2$, and $R^4$ are the same as described above, and $R^3$ represents hydrogen, a hydroxy group, an acyl group, a hydroxyalkyl group, or a carboxyl group;

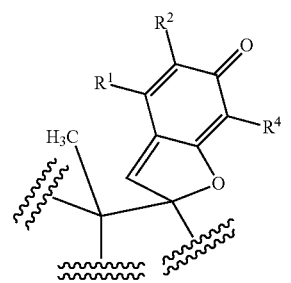

A-3 in the general formula A-3, $R^1$, $R^2$, and $R^4$ are the same as described above.

Of the compounds each represented by the general formula (1), liphagal having the following structure:

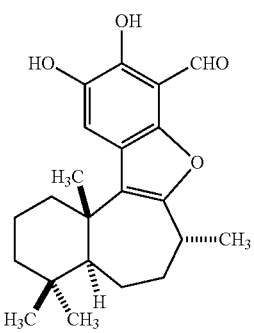

Liphagal is known to have phosphatidylinositol 3-kinase (PI3K) inhibitory activity (Patent Literatures 1 and 2, and Non-patent Literature 1). However, there is no previous report that liphagal inhibits the activity of a kinase other than PI3K, or that liphagal can target many kinases. Accordingly, the effect of the present invention is unpredictable from the related art.

The groups shown in the general formula (1) are specifically as described below.

Examples of the alkyl group may include linear or branched alkyl groups each having 1 to 6 carbon atoms (preferably 1 to 3 carbon atoms, more preferably one carbon atom). More specifically, the alkyl group includes, for example, a methyl group, an ethyl group, a n-propyl group, an isopropyl group, a 2,2-dimethylpropyl group, a 1-ethylpropyl group, a n-butyl group, an isobutyl group, a tert-butyl group, an isopentyl group, a n-pentyl group, and a n-hexyl group.

Examples of the acyl group may include linear or branched acyl groups each having 1 to 6 carbon atoms (preferably 1 to 3 carbon atoms, more preferably one carbon atom). More specifically, the acyl group includes, for example, a formyl group, an acetyl group, a propionyl group, a n-butyryl group, an isobutyryl group, a valeryl group, an isovaleryl group, a pivaloyl group, and a n-hexanoyl group.

Examples of the hydroxyalkyl group may include linear or branched alkyl groups each having a hydroxy group (for example, 1 to 3 hydroxy groups, preferably one hydroxy group) and 1 to 6 carbon atoms (preferably 1 to 3 carbon atoms, more preferably one carbon atom). The hydroxyalkyl group includes, for example, a hydroxymethyl group, a 2-hydroxyethyl group, a 3-hydroxypropyl group, a 2-hydroxypropyl group, a 1-methyl-2-hydroxyethyl group, a 4-hydroxybutyl group, a 3,4-dihydroxybutyl group, a 5-hydroxypentyl group, and a 6-hydroxyhexyl group.

In the general formula (1), it is preferred that at least one (preferably one to three) of $R^1$, $R^2$, $R^3$, $R^4$, and $R^5$ represent at least one kind of substituent selected from the group consisting of a hydroxy group, a hydroxyalkyl group, and a carboxyl group, and it is more preferred that at least one (preferably one to three) of $R^1$, $R^2$, $R^3$, $R^4$, and $R^5$ represent a hydroxy group. In addition, in the general formula (1), it is preferred that at least one (preferably one) of $R^1$, $R^2$, $R^3$, $R^4$, and $R^5$ represent an acyl group.

In a preferred embodiment of the present invention, in the general formula (1), it is preferred that at least one (preferably one or two) of $R^1$, $R^2$, and $R^4$ represent at least one kind of substituent selected from the group consisting of a hydroxy group, a hydroxyalkyl group, and a carboxyl group, at least one (preferably one) thereof represent an acyl group, the rest of $R^1$, $R^2$, and $R^4$ represent hydrogen, $R^3$ represent a hydroxy group or an oxo group (=O), and $R^5$ represent hydrogen or $R^5$ and $R^6$ together form an oxo group (=O); and it is more preferred that at least one (preferably one or two) of $R^1$, $R^2$, and $R^4$ represent a hydroxy group, at least one (preferably one) thereof represent an acyl group, the rest of $R^1$, $R^2$, and $R^4$ represent hydrogen, $R^3$ represent a hydroxy group or an oxo group (=O), and $R^5$ represent hydrogen or $R^5$ and $R^6$ together form an oxo group (=O).

In the present invention, in the general formula (1), $R^6$ is not present (when the carbon atom to which the $R^6$ is to be bonded forms a double bond with another carbon atom adjacent thereto), or forms an oxo group (=O) together with $R^5$.

In the present invention, in the general formula (1), a moiety represented by the following general formula A represents a structure represented by the following general formula A-1, A-2, or A-3:

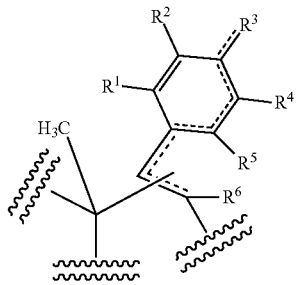

A in the general formula A, $R^1$, $R^2$, $R^3$, $R^4$, $R^5$, and $R^6$ are the same as described above;

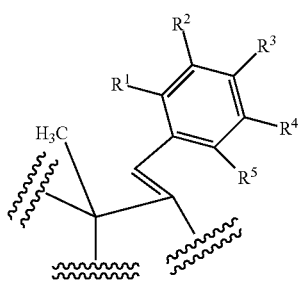

A-1 in the general formula A-1, $R^1$, $R^2$, $R^4$, and $R^5$ are the same as described above, and $R^3$ represents hydrogen, a hydroxy group, an acyl group, a hydroxyalkyl group, or a carboxyl group;

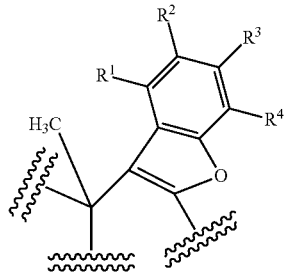

A-2 in the general formula A-2, $R^1$, $R^2$, and $R^4$ are the same as described above, and $R^3$ represents hydrogen, a hydroxy group, an acyl group, a hydroxyalkyl group, or a carboxyl group;

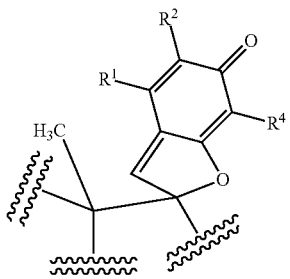

A-3 in the general formula A-3, $R^1$, $R^2$, and $R^4$ are the same as described above.

In one embodiment of the present invention, in the general formula (1), the moiety of the general formula A may have the structure represented by the A-1. That is, in one embodiment of the present invention, an example of the compound represented by the general formula (1) is a compound represented by the following general formula (1-1):

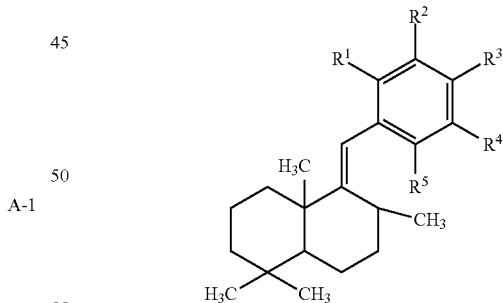

(1-1)

in the general formula (1-1), $R^1$, $R^2$, $R^4$, and $R^5$ are the same as in the general formula (1) above, and $R^3$ represents hydrogen, a hydroxy group, an acyl group, a hydroxyalkyl group, or a carboxyl group. The compound represented by the general formula (1-1) or a salt thereof is preferred because the compound or the salt thereof not only has inhibitory activity against various kinases, but also has relatively high stability.

In the general formula (1-1), it is preferred that at least one (preferably one to three, more preferably three) of $R^1$, $R^2$, $R^3$, $R^4$, and $R^5$ represent at least one kind of substituent selected from the group consisting of a hydroxy group, a hydroxyalkyl group, and a carboxyl group, and it is more preferred that at least one (preferably one to three, more preferably three) of $R^1$, $R^2$, $R^3$, $R^4$, and $R^5$ represent a hydroxy group. In addition, in the general formula (1-1), it is preferred that at least one (preferably one) of $R^1$, $R^2$, $R^3$, $R^4$, and $R^5$ represent an acyl group.

In a preferred embodiment of the present invention, in the general formula (1-1), it is preferred that at least one (preferably one to three, more preferably three) of $R^1$, $R^2$, $R^3$, $R^4$, and $R^5$ represent at least one kind of substituent selected from the group consisting of a hydroxy group, a hydroxyalkyl group, and a carboxyl group, at least one (preferably one) thereof represent an acyl group, and (when the total number of hydroxy groups, hydroxyalkyl groups, carboxyl groups, and acyl groups is 4 or less) the rest of $R^1$, $R^2$, $R^3$, $R^4$, and $R^5$ represent hydrogen; and it is more preferred that at least one (preferably one to three, more preferably three) of $R^1$, $R^2$, $R^3$, $R^4$, and $R^5$ represent a hydroxy group, at least one (preferably one) thereof represent an acyl group, and (when the total number of hydroxy groups and acyl groups is 4 or less) the rest of $R^1$, $R^2$, $R^3$, $R^4$, and $R^5$ represent hydrogen.

In the general formula (1-1), when at least one of $R^1$, $R^2$, $R^3$, $R^4$, and $R^5$ represents at least one kind of substituent selected from the group consisting of a hydroxy group, a hydroxyalkyl group, and a carboxyl group (preferably a hydroxy group), it is preferred that, among $R^1$, $R^2$, $R^3$, $R^4$, and $R^5$, at least $R^1$, $R^3$, and $R^4$ each represent at least one kind of substituent selected from the group consisting of a hydroxy group, a hydroxyalkyl group, and a carboxyl group (preferably a hydroxy group). In the general formula (1-1), when at least one of $R^1$, $R^2$, $R^3$, $R^4$, and $R^5$ represents an acyl group, it is preferred that, among $R^1$, $R^2$, $R^3$, $R^4$, and $R^5$, at least $R^2$ represent an acyl group.

In the general formula (1-1), it is preferred that $R^1$, $R^3$, and $R^4$ each represent at least one kind of substituent selected from the group consisting of a hydroxy group, a hydroxyalkyl group, and a carboxyl group (preferably a hydroxy group), $R^2$ represent an acyl group, and $R^5$ represent hydrogen.

In the present invention, the steric structure of the compound represented by the general formula (1-1) or the salt thereof is not particularly limited, but for example, a compound represented by the following general formula (1-1') or a salt thereof is preferred:

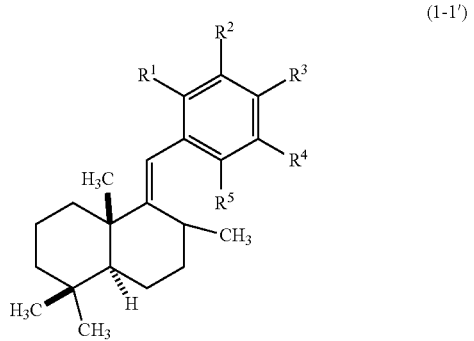

(1-1')

in the general formula (1-1'), $R^1$, $R^2$, $R^3$, $R^4$, and $R^5$ are the same as in the general formula (1-1) above.

In one embodiment of the present invention, in the general formula (1), the moiety of the general formula A may have the structure represented by the A-2. That is, in one embodiment of the present invention, an example of the compound represented by the general formula (1) is a compound represented by the following general formula (1-2):

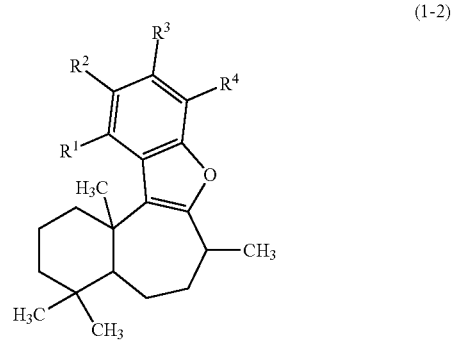

(1-2)

in the general formula (1-2), $R^1$, $R^2$, $R^3$, and $R^4$ are the same as in the general formula (1) above, and $R^3$ represents hydrogen, a hydroxy group, an acyl group, a hydroxyalkyl group, or a carboxyl group.

In the general formula (1-2), it is preferred that at least one (preferably one to three, more preferably two) of $R^1$, $R^2$, $R^3$, and $R^4$ represent at least one kind of substituent selected from the group consisting of a hydroxy group, a hydroxyalkyl group, and a carboxyl group, and it is more preferred that at least one (preferably one to three, more preferably two) of $R^1$, $R^2$, $R^3$, and $R^4$ represent a hydroxy group. In addition, in the general formula (1-2), it is preferred that at least one (preferably one) of $R^1$, $R^2$, $R^3$, and $R^4$ represent an acyl group.

In a preferred embodiment of the present invention, in the general formula (1-2), it is preferred that at least one (preferably one to three, more preferably two) of $R^1$, $R^2$, $R^3$, and $R^4$ represent at least one kind of substituent selected from the group consisting of a hydroxy group, a hydroxyalkyl group, and a carboxyl group, at least one (preferably one) thereof represent an acyl group, and (when the total number of hydroxy groups, hydroxyalkyl groups, carboxyl groups, and acyl groups is 3 or less) the rest of $R^1$, $R^2$, $R^3$, and $R^4$ represent hydrogen; and it is more preferred that at least one (preferably one to three, more preferably two) of $R^1$, $R^2$, $R^3$, and $R^4$ represent a hydroxy group, at least one (preferably one) thereof represent an acyl group, and (when the total number of hydroxy groups and acyl groups is 4 or less) the rest of $R^1$, $R^2$, $R^3$, and $R^4$ represent hydrogen.

In the general formula (1-2), when at least one of $R^1$, $R^2$, $R^3$, and $R^4$ represents at least one kind of substituent selected from the group consisting of a hydroxy group, a hydroxyalkyl group, and a carboxyl group (preferably a hydroxy group), it is preferred that, among $R^1$, $R^2$, $R^3$, and $R^4$, at least $R^2$ and $R^3$ each represent at least one kind of substituent selected from the group consisting of a hydroxy group, a hydroxyalkyl group, and a carboxyl group (preferably a hydroxy group). In the general formula (1-1), when at least one of $R^1$, $R^2$, $R^3$, and $R^4$ represents an acyl group, it is preferred that, among $R^1$, $R^2$, $R^3$, and $R^4$, at least $R^4$ represent an acyl group.

In the general formula (1-2), it is preferred that $R^1$ represent hydrogen, $R^2$ and $R^3$ each represent at least one kind of substituent selected from the group consisting of a hydroxy group, a hydroxyalkyl group, and a carboxyl group (preferably a hydroxy group), and $R^4$ represent an acyl group.

In the present invention, the steric structure of the compound represented by the general formula (1-2) or the salt thereof is not particularly limited, but for example, a compound represented by the following general formula (1-2') or a salt thereof is preferred:

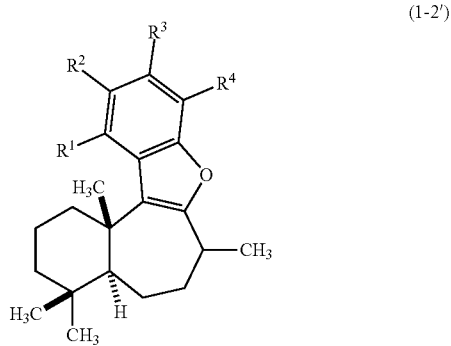

(1-2')

in the general formula (1-2'), $R^1$, $R^2$, $R^3$, and $R^4$ are the same as in the general formula (1-2) above.

In one embodiment of the present invention, in the general formula (1), the moiety of the general formula A may have the structure represented by the A-3. That is, in one embodiment of the present invention, an example of the compound represented by the general formula (1) is a compound represented by the following general formula (1-3):

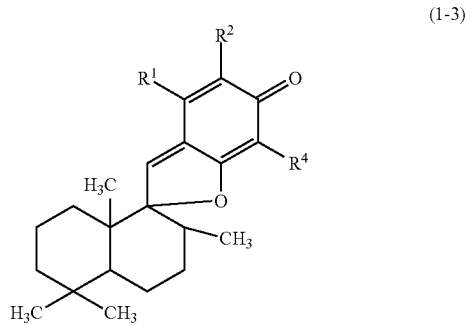

(1-3)

in the general formula (1-3), $R^1$, $R^2$, and $R^4$ are the same as in the general formula (1) above.

In the general formula (1-3), it is preferred that at least one (preferably one to three, more preferably one) of $R^1$, $R^2$, and $R^4$ represent at least one kind of substituent selected from the group consisting of a hydroxy group, a hydroxyalkyl group, and a carboxyl group, and it is more preferred that at least one (preferably one to three, more preferably one) of $R^1$, $R^2$, and $R^4$ represent a hydroxy group. In addition, in the general formula (1-3), it is preferred that at least one (preferably one) of $R^1$, $R^2$, and $R^4$ represent an acyl group.

In a preferred embodiment of the present invention, in the general formula (1-3), it is preferred that one or two (preferably one) of $R^1$, $R^2$, and $R^4$ represent at least one kind of substituent selected from the group consisting of a hydroxy group, a hydroxyalkyl group, and a carboxyl group, one or two (preferably one) thereof represent an acyl group, and when the total number of hydroxy groups, hydroxyalkyl groups, carboxyl groups, and acyl groups is 2, the rest of $R^1$, $R^2$, and $R^4$ represent hydrogen; and it is more preferred that one or two (preferably one) of $R^1$, $R^2$, and $R^4$ represent a hydroxy group, one or two (preferably one) thereof represent an acyl group, and when the total number of hydroxy groups and acyl groups is 2, the rest of $R^1$, $R^2$, and $R^4$ represent hydrogen.

In the general formula (1-3), when one or two of $R^1$, $R^2$, and $R^4$ represent(s) at least one kind of substituent selected from the group consisting of a hydroxy group, a hydroxyalkyl group, and a carboxyl group (preferably a hydroxy group), it is preferred that, among $R^1$, $R^2$, and $R^4$, at least $R^2$ represent at least one kind of substituent selected from the group consisting of a hydroxy group, a hydroxyalkyl group, and a carboxyl group (preferably a hydroxy group). In the general formula (1-3), when one or two of $R^1$, $R^2$, and $R^4$ represent(s) an acyl group, it is preferred that, among $R^1$, $R^2$, and $R^4$, at least $R^4$ represent an acyl group.

In the general formula (1-3), it is preferred that $R^1$ represent hydrogen, $R^2$ represent at least one kind of substituent selected from the group consisting of a hydroxy group, a hydroxyalkyl group, and a carboxyl group (preferably a hydroxy group), and $R^4$ represent an acyl group.

In the present invention, the steric structure of the compound represented by the general formula (1-3) or the salt thereof is not particularly limited, but for example, a compound represented by the following general formula (1-3') or a salt thereof is preferred:

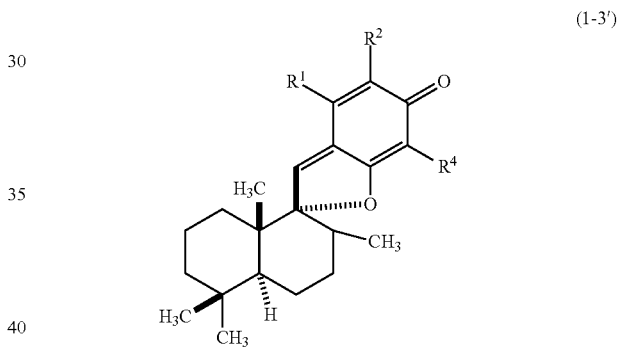

(1-3')

in the general formula (1-3'), $R^1$, $R^2$, and $R^4$ are the same as in the general formula (1-3) above.

The compound represented by the general formula (1) or the salt thereof may be produced by a method described in Kamishima et al. European Journal of Organic Chemistry, 3443-3450 (2014) (Non-patent Literature 3), a method described in FIG. 3, a method described in Examples to be described later, or a method similar thereto.

Figure 3:
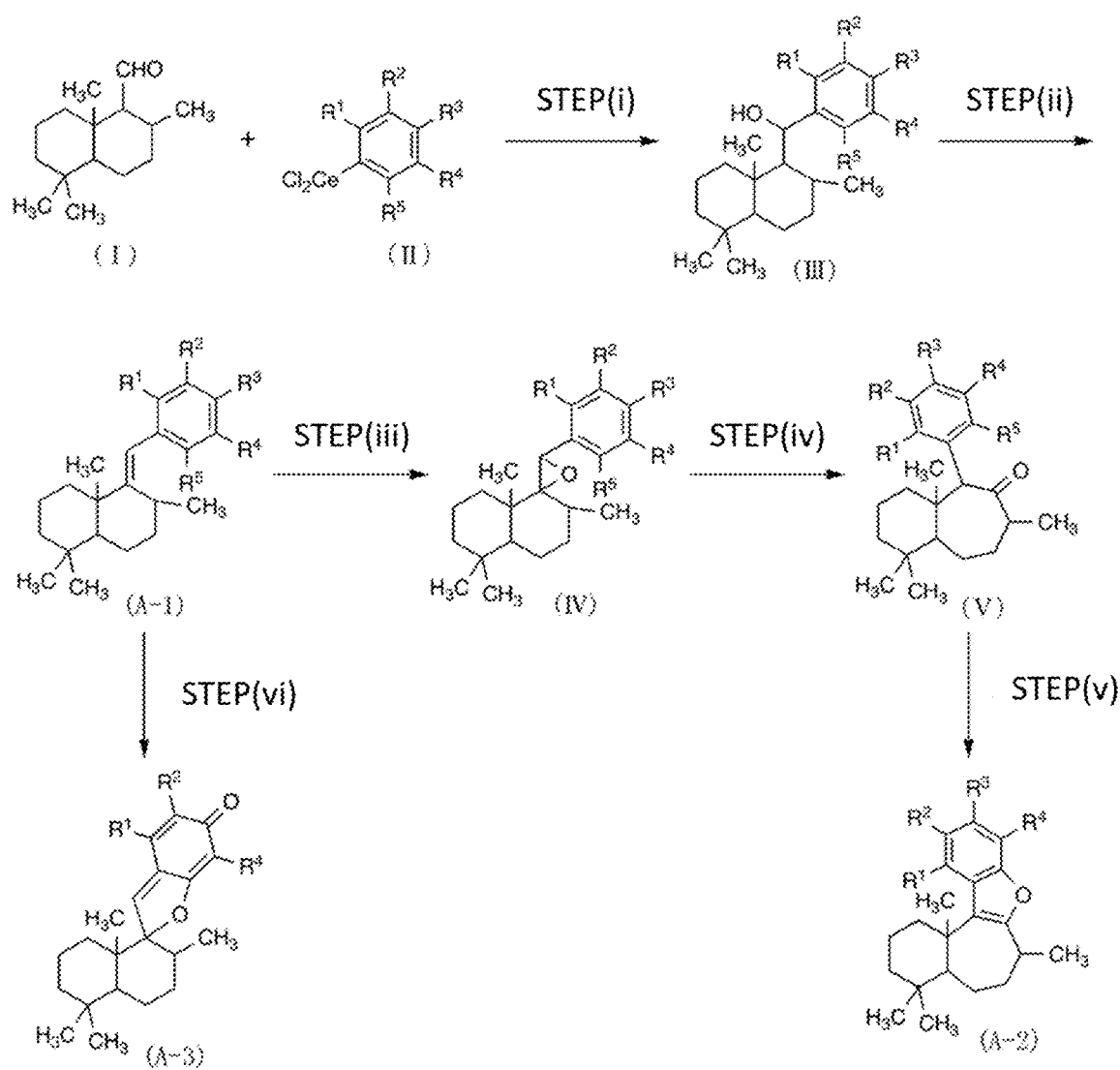
FIG. 3 is a scheme for illustrating the outline of an example of a production method for a compound represented by the general formula (1) or a salt thereof.

Now, a description is made with reference to FIG. 3. In FIG. 3, $R^1$, $R^2$, $R^3$, $R^4$, and $R^5$ are as described above for the general formula (1). However, in order to allow each reaction to proceed, each group may be appropriately protected with and deprotected of, for example, a protective group known in the field of organic synthesis. First, in Step (i), decalin aldehyde (I) prepared from (+)-sclareolide may be subjected to a reaction with an arylcerium reagent (II) to afford an adduct (III). In Step (ii), the adduct (III) may be subjected to a dehydration reaction, followed by, for example, the introduction of a substituent to the aromatic ring moiety and the removal of a protective group, to afford a compound (A-1). In Step (iii), a double bond of the compound (A-1) may be subjected to epoxidation to afford an epoxide (IV). In Step (iv), the compound (IV) may be subjected to a ring expansion reaction involving the cleavage of its epoxy ring and subsequent semipinacol rearrangement, to afford a cycloheptanone derivative (V). In Step (v), the compound (V) was subjected to the formation of a furan ring to synthesize a compound (A-2). Meanwhile, in Step (vi), the compound (A-1) was subjected to the formation of a spiro ring to synthesize a compound (A-3). In each of the above-mentioned steps, conditions such as: a blending ratio between the starting materials; the kind and amount of a solvent; the kind and amount of a catalyst; a reaction time; and a reaction temperature may be appropriately set with reference to the description of Examples of the present application.

In a typical embodiment of the present invention, the compound represented by the general formula (1) or the salt thereof is used as an inhibitor for at least one kind of kinase selected from the group consisting of cyclin-dependent kinase 7 (CDK7), cyclin-dependent kinase 4 (CDK4), cyclin-dependent kinase 6 (CDK6), Proviral Integrations of Moloney virus 2 (PIM2), testis-specific serine kinase 3 (TSSK3), mammalian STE20-like protein kinase 4 (MST4), never in mitosis gene a (NIMA)-related kinase 6 (NEK6), mitogen-activated protein kinase kinase kinase (MAP3K), mammalian STE20-like protein kinase 3 (MST3), discoidin domain receptor tyrosine kinase 1 (DDR1), sphingosine kinase 1 (SPHK1), calcium/calmodulin-dependent protein kinase I (CaMK1), aurora kinase A (AurA), PTK6 protein tyrosine kinase 6 (BRK), calcium/calmodulin-dependent protein kinase IV (CaMK4), and Proviral Integrations of Moloney virus 1 (PIM1).

Of those, CDK7, CDK4, and CDK6 are known to be kinases associated with the cell cycle. Through inhibition of any one point in the cell cycle, the suppression of proliferation of tumor cells and the like can be expected. In a preferred embodiment of the present invention, the inhibitor of the present invention may be used as an inhibitor for at least one kind of kinase selected from the group consisting of CDK7, CDK4, and CDK6 out of the above-mentioned kinases.

In addition, in a preferred embodiment, the inhibitor of the present invention may be used as an inhibitor for the above-mentioned kinases and an inhibitor for PI3K. PI3K is a kinase involved in the PI3K/AKT pathway, which is a signaling pathway involved in the survival and proliferation of cells. The PI3K/AKT pathway is abnormally activated in a constitutive manner in a variety of cancer types, and hence serves as a drug target for cancer treatment. Therefore, the inhibitor for: at least one kind of kinase selected from the group consisting of CDK7, CDK4, CDK6, PIM2, TSSK3, MST4, NEK6, MAP3K, MST3, DDR1, SPHK1, CaMK1, AurA, BRK, CaMK4, and PIM1; and PI3K according to such embodiment of the present invention is preferred. In addition, of the above-mentioned kinases, it is known that cells in which PIM2 has high kinase activity have shown high PI3K resistance. Therefore, an inhibitor showing inhibitory activity against PIM2 as well as PI3K can be expected to have an effect even on cells having high resistance to PI3K, and hence the inhibitor of the present invention is preferably used as an inhibitor for at least PIM2 and PI3K out of the above-mentioned kinases.

In addition, the mechanism of proliferation of cancer cells is complicated, and having a plurality of target molecules contributes to an effect as a pharmaceutical agent in some cases. In fact, multi-targeted kinase inhibitors have been used in clinical settings. Therefore, the inhibitor of the present invention is also preferably used as a multi-targeted kinase inhibitor, specifically, as an inhibitor for two or more kinds (preferably three or more kinds, more preferably four or more kinds) of kinases selected from the group consisting of CDK7, CDK4, CDK6, PIM2, TSSK3, MST4, NEK6, MAP3K, MST3, DDR1, SPHK1, CaMK1, AurA, BRK, CaMK4, and PIM1, or for two or more kinds (preferably three or more kinds, more preferably four or more kinds, still more preferably five or more kinds) of kinases out of PI3K and kinases selected from the group consisting of CDK7, CDK4, CDK6, PIM2, TSSK3, MST4, NEK6, MAP3K, MST3, DDR1, SPHK1, CaMK1, AurA, BRK, CaMK4, and PIM1.

The inhibitor of the present invention may be used as a preventive or therapeutic agent for a disease (e.g., cancer) that is treatable through inhibition of at least one kind of kinase selected from the group consisting of CDK7, CDK4, CDK6, PIM2, TSSK3, MST4, NEK6, MAP3K, MST3, DDR1, SPHK1, CaMK1, AurA, BRK, CaMK4, and PIM1. The preventive or therapeutic agent of the present invention may be particularly used for the prevention or treatment of cancers, such as skin cancer, mesothelioma, lung cancer, stomach cancer, liver cancer, colorectal cancer, breast cancer, esophageal cancer, pancreatic cancer, uterine cancer (cervical cancer and endometrial cancer), ovarian cancer, skin cancer, urological cancer, head and neck cancer, cancer of unknown primary site, hematologic malignancies (leukemia and lymphoma), and bone soft tissue sarcoma.

In addition, when used also as an inhibitor for PI3K, the inhibitor of the present invention may be used particularly for the prevention or treatment of breast cancer, endometrial cancer, urological cancer, colorectal cancer, ovarian cancer, head and neck cancer, lung cancer, and the like, in which mutations in PIK3CA gene have been frequently reported. In addition, such embodiment is preferred because a therapeutic effect on so-called refractory cancer, on which the effect of any other treatment is not found or is low, can be expected.

Further, of the compounds each represented by the general formula (1) or the salts thereof, the compound represented by the general formula (1-1) has not been known for inhibitory activity against CDK7, CDK4, CDK6, PIM2, TSSK3, MST4, NEK6, MAP3K, MST3, DDR1, SPHK1, CaMK1, AurA, BRK, CaMK4, and PIM1, and besides, has not been known for inhibitory activity against PI3K.

Therefore, the present invention also provides a phosphatidylinositol 3-kinase (PI3K) inhibitor containing the compound represented by the general formula (1-1) or the salt thereof. The PI3K inhibitor containing the compound represented by the general formula (1-1) or the salt thereof may be used as a preventive or therapeutic agent for a disease (e.g., cancer) that is treatable through inhibition of PI3K. The PI3K inhibitor may be used particularly for the prevention or treatment of breast cancer, endometrial cancer, urological cancer, colorectal cancer, ovarian cancer, head and neck cancer, lung cancer, and the like, in which mutations in PIK3CA gene have been frequently reported. In addition, such embodiment is preferred because a therapeutic effect on so-called refractory cancer, on which the effect of any other treatment is not found or is low, can be expected.

The present invention also provides the following novel compound and a salt thereof:

a compound represented by the following general formula (1) or a salt thereof:

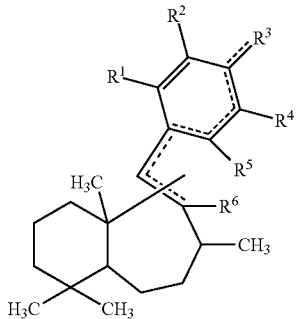
(1)

in the general formula (1), $R^1$, $R^2$, $R^4$, and $R^5$ are identical to or different from each other, and each represent hydrogen, a hydroxy group, an acyl group, a hydroxyalkyl group, or a carboxyl group, $R^3$ represents hydrogen, a hydroxy group, an acyl group, a hydroxyalkyl group, a carboxyl group, or an oxo group (=O), $R^5$ and $R^6$ may together form an oxo group (=O), ===== represents a single bond or a double bond, and a moiety represented by the following general formula A represents the following A-1, A-2, or A-3:

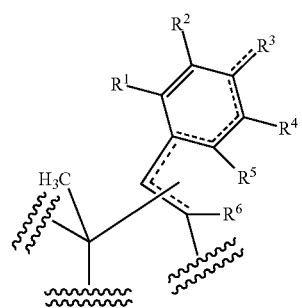
A in the general formula A, $R^1$, $R^2$, $R^3$, $R^4$, $R^5$, and $R^6$ are the same as described above;

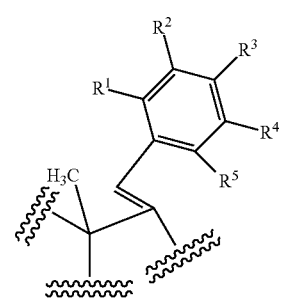
A-1 in the general formula A-1, $R^1$, $R^2$, $R^4$, and $R^5$ are the same as described above, and $R^3$ represents hydrogen, a hydroxy group, an acyl group, a hydroxyalkyl group, or a carboxyl group;

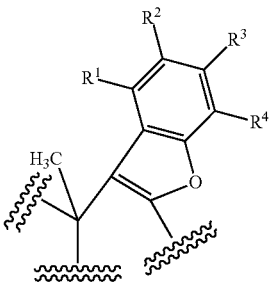
A-2 in the general formula A-2, $R^1$, $R^2$, and $R^4$ are the same as described above, and $R^3$ represents hydrogen, a hydroxy group, an acyl group, a hydroxyalkyl group, or a carboxyl group;

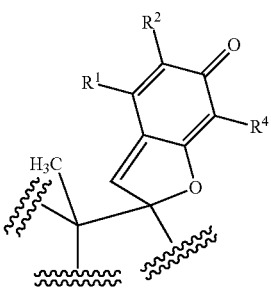
A-3 in the general formula A-3, $R^1$, $R^2$, and $R^4$ are the same as described above, provided that a compound represented by

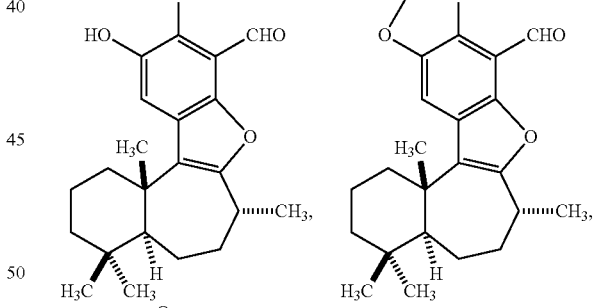

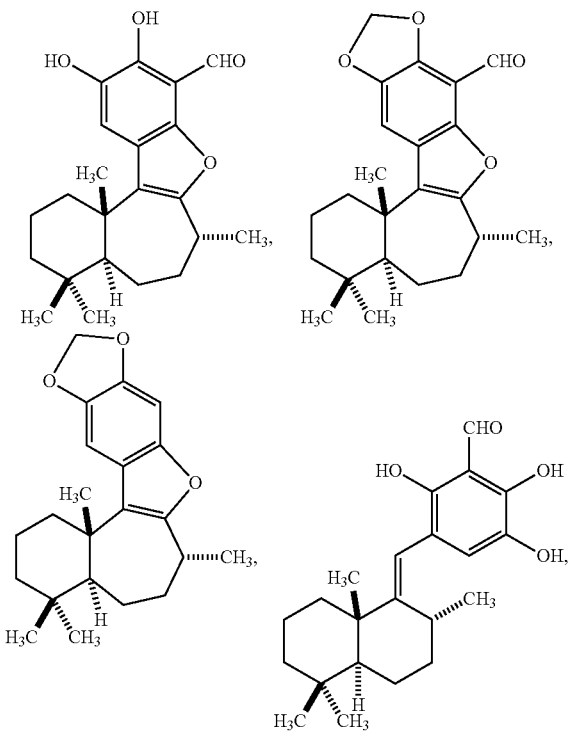

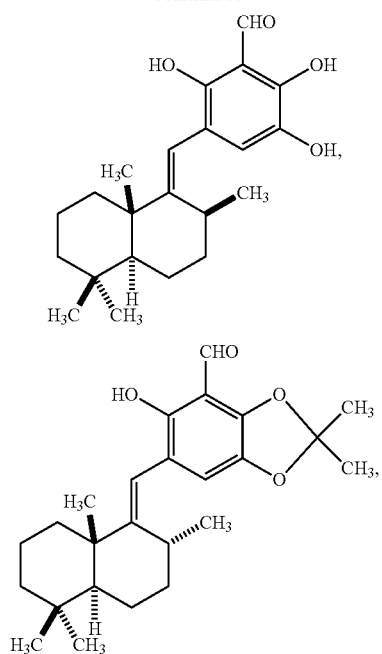

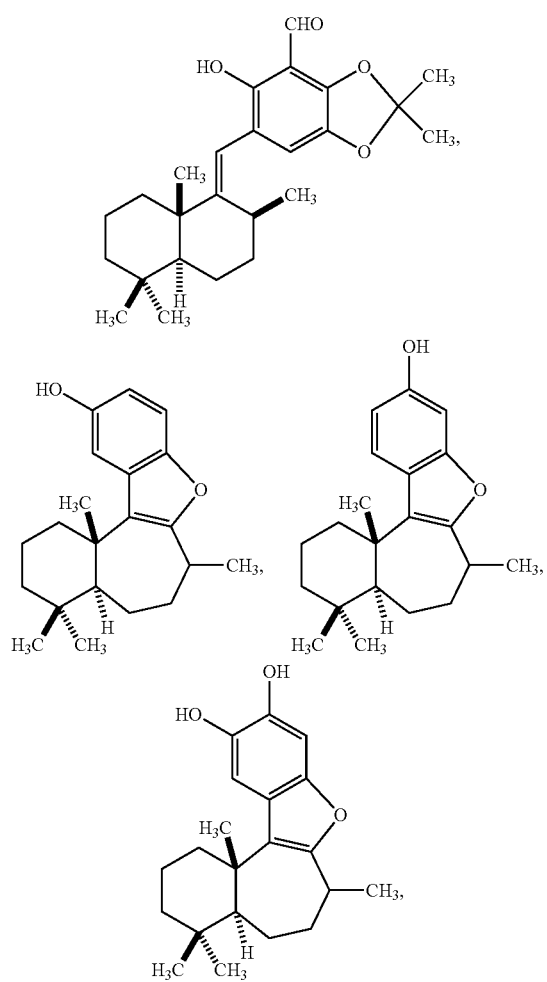

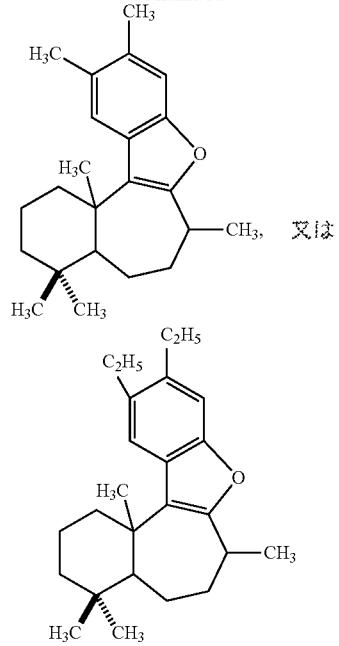

or a salt thereof is excluded.

Such novel compound is encompassed in the compound represented by the general formula (1) or the salt thereof, and hence may be used in the same manner as the inhibitor of the present invention. As preferred chemical structures of the novel compound, the same ones as those described above for the compound represented by the general formula (1) serving as the active ingredient in the inhibitor for CDK7 and the like of the present invention may be given except that the above-mentioned specific compounds are excluded.

When the compound represented by the general formula (1) or the salt thereof serving as the active ingredient of the present invention has an isomer, such as an optical isomer, a stereoisomer, or a regioisomer, the present invention may encompass both an invention using any of the isomers and an invention using a mixture of a variety of isomers, unless it is clearly specified which of the isomers is used.

The salt of the compound represented by the general formula (1) serving as the active ingredient of the present invention encompasses an acid addition salt and a salt with a base. Specific examples of the acid addition salt include: inorganic acid salts, such as a hydrochloride salt, a hydrobromide salt, a hydroiodide salt, a sulfate salt, a perchlorate salt, and a phosphate salt; organic acid salts, such as an oxalate salt, a malonate salt, a succinate salt, a maleate salt, a fumarate salt, a lactate salt, a malate salt, a citrate salt, a tartrate salt, a benzoate salt, a trifluoroacetate salt, an acetate salt, a methanesulfonate salt, a p-toluenesulfonate salt, and a trifluoromethanesulfonate salt; and acidic amino acid salts, such as a glutamate salt and an aspartate salt. Specific examples of the salt with a base include: alkali metal salts and alkaline earth metal salts, such as a sodium salt, a potassium salt, and a calcium salt; salts with organic bases, such as a pyridine salt and a triethylamine salt; and salts with basic amino acids, such as lysine and arginine. In addition, when the compound represented by the general formula (1) serving as the active ingredient of the present invention is a cation, the salt of the compound represented by the general formula (1) also encompasses halides (e.g., a chloride) and the like.

The compound represented by the general formula (1) serving as the active ingredient of the present invention may be present in the form of a hydrate or a solvate, and hence the compound serving as the active ingredient of the present invention also encompasses such hydrate and solvate.

A solvent for forming the solvate is exemplified by: alcohols, such as ethanol and propanol; organic acids, such as acetic acid; esters, such as ethyl acetate; ethers, such as tetrahydrofuran and diethyl ether; ketones, such as acetone; and DMSO.

In the present invention, the compound represented by the general formula (1) or the salt thereof serving as the active ingredient of the present invention may be used alone as a kinase inhibitor, or may be used as a pharmaceutical composition in combination with any of various pharmaceutically acceptable carriers (e.g., a tonicity agent, a chelating agent, a stabilizing agent, a pH regulator, a preservative, an antioxidant, a solubilizing agent, or a thickening agent).

Examples of the tonicity agent include: sugars, such as glucose, trehalose, lactose, fructose, mannitol, xylitol, and sorbitol; polyhydric alcohols, such as glycerin, polyethylene glycol, and propylene glycol; and inorganic salts, such as sodium chloride, potassium chloride, and calcium chloride. Those tonicity agents may be used alone or in combination thereof.

Examples of the chelating agent include edetate salts, such as edetate disodium, edetate calcium disodium, edetate trisodium, edetate tetrasodium, and edetate calcium, an ethylenediaminetetraacetate salt, nitrilotriacetic acid or a salt thereof, sodium hexametaphosphate, and citric acid. Those chelating agents may be used alone or in combination thereof.

An example of the stabilizing agent is sodium bisulfite.

Examples of the pH regulator include acids, such as hydrochloric acid, carbonic acid, acetic acid, and citric acid, and further include: alkali metal hydroxides, such as sodium hydroxide and potassium hydroxide; alkali metal carbonates or alkali metal bicarbonates, such as sodium carbonate; alkali metal acetates, such as sodium acetate; alkali metal citrates, such as sodium citrate; and bases, such as trometamol. Those pH regulators may be used alone or in combination thereof.

Examples of the preservative include sorbic acid, potassium sorbate, parahydroxybenzoate esters, such as methyl parahydroxybenzoate, ethyl parahydroxybenzoate, propyl parahydroxybenzoate, and butyl parahydroxybenzoate, chlorhexidine gluconate, quaternary ammonium salts, such as benzalkonium chloride, benzethonium chloride, and cetylpyridinium chloride, alkylpolyaminoethylglycine, chlorobutanol, polyquad, polyhexamethylene biguanide, and chlorhexidine, Those preservatives may be used alone or in combination thereof.

Examples of the antioxidant include sodium bisulfite, dry sodium sulfite, sodium pyrosulfite, and mixed tocopherol concentrate. Those antioxidants may be used alone or in combination thereof.

Examples of the solubilizing agent include sodium benzoate, glycerin, D-sorbitol, glucose, propylene glycol, hydroxypropylmethylcellulose, polyvinylpyrrolidone, macrogol, and D-mannitol. Those solubilizing agents may be used alone or in combination thereof.

Examples of the thickening agent include polyethylene glycol, methylcellulose, ethylcellulose, carmellose sodium, xanthan gum, sodium chondroitin sulfate, hydroxyethylcellulose, hydroxypropylcellulose, hydroxypropylmethylcellulose, polyvinylpyrrolidone, and polyvinyl alcohol. Those thickening agents may be used alone or in combination thereof.

In addition, the pharmaceutical composition may further contain, in addition to the compound represented by the general formula (1) or the salt thereof, a compound known to have a preventive or therapeutic action on a disease, such as any of the above-mentioned cancers. Examples of the compound known to have a preventive or therapeutic action on a disease, such as any of the above-mentioned cancers, include a poly ADP ribose polymerase (PARE)) inhibitor and a histone deacetylase (HDAC) inhibitor. Those compounds may be used alone or in combination thereof.

In the embodiment of the pharmaceutical composition, the content of the compound represented by the general formula (1) or the salt thereof in the composition is not particularly limited, and may be appropriately set within, for example, conditions such as 90 mass % or more, 70 mass % or more, 50 mass % or more, 30 mass % or more, 10 mass % or more, 5 mass % or more, and 1 mass % or more in terms of the content of the compound represented by the general formula (1).

A dosage form is not particularly limited, and examples thereof may include various dosage forms including: orally administered agents, such as tablets, pills, capsules, powders, granules, and syrups; and parenterally administered agents, such as injections (e.g., intravenous injections, intramuscular injections, and local injections), gargles, intravenous drips, external preparations (ointments, creams, patches, and inhalants), and suppositories. Of those dosage forms, preferred examples include orally administered agents (e.g., tablets, pills, capsules, powders, granules, and syrups), injections (e.g., intravenous injections, intramuscular injections, and local injections), gargles, intravenous drips, and external preparations (ointments, creams, patches, and inhalants).

In the present invention, the dose of the compound represented by the general formula (1) or the salt thereof varies depending on, for example, an administration route and the age, body weight, or symptom of a patient, and hence cannot be uniquely defined. However, the dose only needs to be such an amount that a daily dose for adults is generally about 5,000 mg or less, preferably about 1,000 mg or less, more preferably 500 mg or less in terms of the dose of the compound represented by the general formula (1). The lower limit of the dose of the compound represented by the general formula (1) or the salt thereof is also not particularly limited, and may be appropriately set within, for example, such a range that a daily dose for adults is generally 1 mg or more, preferably 10 mg or more, more preferably 100 mg or more in terms of the dose of the compound represented by the general formula (1). When administered once daily, the compound or the salt thereof only needs to be contained in the above-mentioned amount in a single dose. When administered three times daily, the compound or the salt thereof only needs to be contained in an amount corresponding to one-third of the above-mentioned amount in a single dose.

The kinase inhibitor, or preventive or therapeutic agent of the present invention is administered to patients, such as mammals. Examples of the mammals include humans, monkeys, mice, rats, rabbits, cats, dogs, pigs, cattle, horses, and sheep. The kinase inhibitor of the present invention may be used not only for the purpose of preventing or treating a disease, but also for, for example, the purpose of research and development, such as drug development.

The present invention is more specifically described below by way of Examples. However, the present invention is not limited thereto.

EXAMPLES

[Production Example 1] Synthesis of LG-5

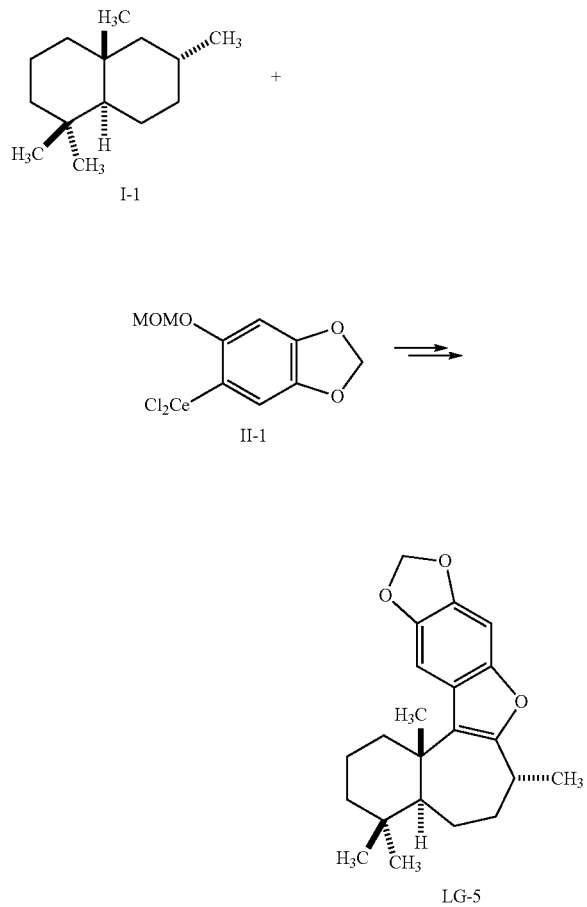

A compound (LG-5) was synthesized using (1S,2R,4aS,8aS)-2,5,5,8a-tetramethyldecahydronaphthalene-1-carbaldehyde (I-1) and an arylcerium reagent (II-1) as starting materials in accordance with a method described in the literature [Kamishima et al. European Journal of Organic Chemistry, 3443-3450 (2014) (Non-patent Literature 3)].

$^1$H NMR (400 MHz, CDCl$_3$): δ=0.94 (s, 3H), 0.97 (s, 3H), 1.20-1.28 (m, 1H), 1.35 (s, 3H), 1.40 (d, J=7.3 Hz, 3H), 1.44-1.53 (m, 4H), 1.57-1.86 (m, 4H), 2.12-2.19 (m, 1H), 2.56 (br d, J=12.7 Hz, 1H), 3.13-3.22 (m, 1H), 5.93 (s, 2H), 6.85 (s, 1H), 7.12 (s, 1H) ppm.

$^{13}$C NMR (100 MHz, CDCl$_3$): δ=18.8, 20.0, 22.0, 22.1, 24.1, 33.3, 33.6, 34.8, 35.1, 39.5, 40.1, 42.0, 53.6, 92.8, 101.0, 101.3, 121.4, 125.6, 143.1, 144.4, 148.7, 156.2 ppm. IR (KBr): ν=2927, 2867, 2359, 2335, 1500, 1463, 1339, 1312, 1290, 1280, 1123, 1099, 1079, 999, 978, 904, 840, 787, 754, 713, 698, 668 cm$^{-1}$. HRMS (EI): calcd for C$_{22}$H$_{28}$O$_3$ [M]$^+$ 340.2038; found 340.2042.

[Production Example 2] Synthesis of LG-6

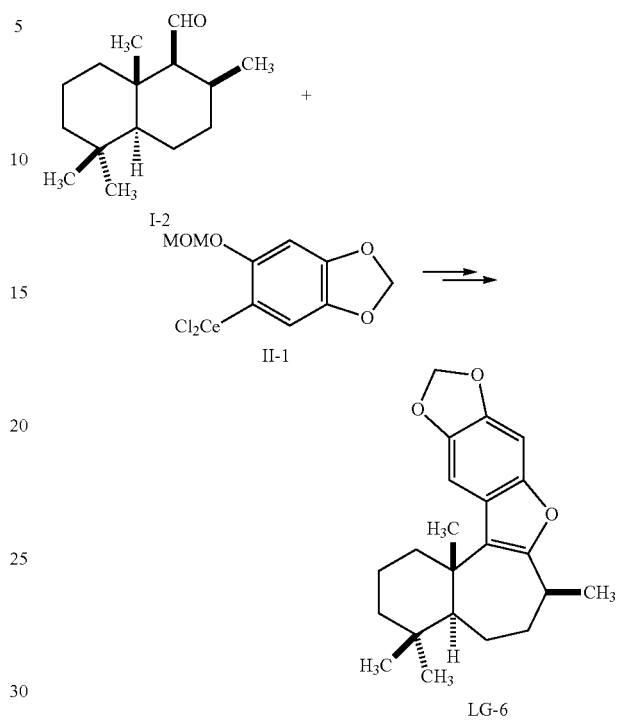

The synthesis of a compound (LG-6) was performed in the same manner as the synthesis of LG-5 except that a (1S,2S,4aS,8aS)-isomer (I-2) was used in place of (1S,2R,4aS,8aS)-2,5,5,8a-tetramethyldecahydronaphthalene-1-carbaldehyde (I-1) as a starting material.

$^1$H NMR (400 MHz, CDCl$_3$): δ=0.95 (s, 3H), 0.97 (s, 3H), 1.16-1.30 (m, 2H), 1.33 (d, J=12.2 Hz, 3H), 1.38 (s, 3H), 1.41-1.56 (m, 2H), 1.62-1.94 (m, 6H), 2.52 (d, J=37.6 Hz, 1H), 3.18-3.33 (m, 1H), 5.92 (d, J=8.3 Hz, 2H), 6.87 (s, 1H), 7.07 (s, 1H) ppm. $^{13}$C NMR (100 MHz, CDCl$_3$): δ=18.7, 18.9, 20.1, 22.4, 22.8, 31.0, 33.8, 34.5, 36.0, 39.3, 40.0, 42.1, 50.2, 93.1, 100.9, 101.0, 121.6, 125.0, 143.1, 144.3, 148.6, 155.0 ppm. IR (neat): 2931, 2360, 2341, 1541, 1507, 1460, 1289, 1220, 1153, 1040948, 844, 772, 668 cm$^{-1}$. HRMS (EI): calcd for C$_{24}$H$_{34}$O$_4$ [M]$^+$ 340.20; found 340.2047.

[Production Example 3] Synthesis of LG-3

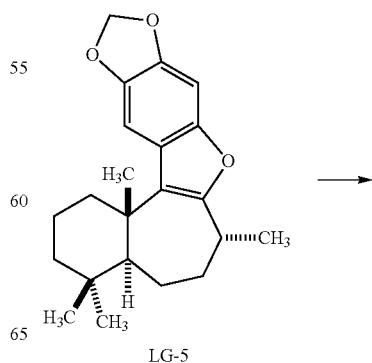

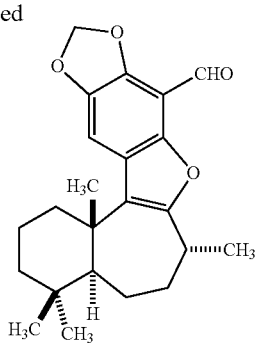

LG-3

A compound (LG-3) was synthesized in accordance with a method described in the literature [Kamishima et al. European Journal of Organic Chemistry, 3443-3450 (2014) (Non-patent Literature 3)]. $^1$H NMR. (400 MHz, CDCl$_3$): δ=0.95 (s, 3H), 0.99 (s, 3H), 1.21-1.29 (m, 1H), 1.35 (s, 3H), 1.45 (d, J=7.3 Hz, 3H), 1.50-1.89 (m, 8H), 2.15-2.21 (m, 1H), 2.50 (br d, J=13.2 Hz, 1H), 3.22-3.30 (m, 1H), 6.12 (s, 2H), 7.36 (s, 1H), 10.47 (s, 1H) ppm. $^{13}$C NMR (100 MHz, CDCl$_3$): δ=18.8, 20.2, 21.9, 22.0, 24.1, 33.3, 33.7, 34.8, 35.0, 39.5, 40.2, 41.9, 53.6, 102.8, 106.0, 107.4, 122.0, 125.5, 144.0, 144.9, 148.0, 157.5, 185.9 ppm. IR (neat): ν=2929, 2868, 2356, 2343, 1693, 1626, 1606, 1500, 1405, 1379, 1157, 1129, 1102, 1030, 998, 971, 811, 714, 680, 654 cm$^{-1}$. HRMS (EI): calcd for C$_{23}$H$_{28}$O$_4$ [M]$^+$ 368.1988; found 368.2005.

[Production Example 4] Synthesis of LG-4

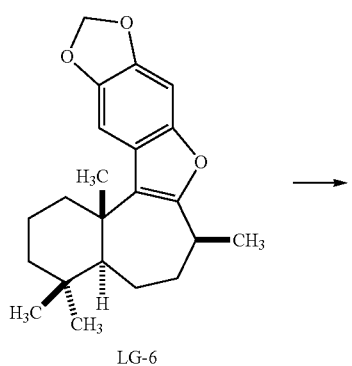

LG-6

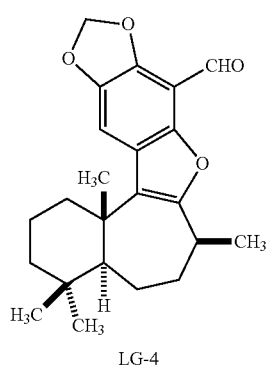

LG-4

The synthesis of a compound (LG-4) was performed in the same manner as the synthesis of LG-3 except that the compound (LG-6) was used in place of the compound (LG-5) as a starting material.

$^1$H NMR (400 MHz, CDCl$_3$): δ=0.90-0.92 (m, 2H), 0.96 (s, 3H), 0.99 (s, 3H), 1.11-1.28 (m, 1H), 1.39 (s, 3H), 1.39 (d, J=6.8 Hz, 3H), 1.40-1.94 (m, 7H), 2.46 (d, J=13.2 Hz, 1H), 3.29-3.34 (m, 1H), 6.12 (s, 1H), 7.31 (s, 1H), 10.48 (s, 1H) ppm. $^{13}$C NMR (100 MHz, CDCl$_3$): δ=18.6, 18.9, 20.3, 22.3, 22.8, 31.1, 33.7, 34.5, 35.8, 39.2, 40.2, 42.0, 50.2, 102.8, 106.2, 106.9, 122.1, 124.9, 144.0, 144.8, 147.8, 156.2, 185.8 ppm. IR (neat): ν=2928, 2353, 1692, 1624, 1458, 1369, 1294, 1186, 1100, 1068, 1005, 929, 844, 754, 661, 632, 607 cm$^{-1}$. HRMS (EI): calcd for C$_{24}$H$_{34}$O$_4$ [M]$^+$ 368.20; found 368.1989.

[Production Example 5] Synthesis of LG-1

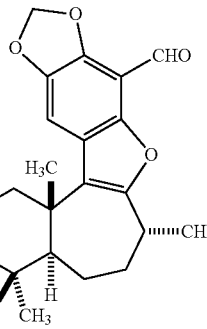

LG-3

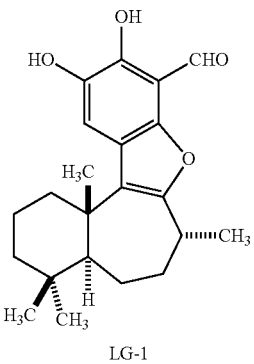

LG-1

A compound (LG-1) was synthesized in accordance with a method described in the literature [Kamishima et al. European Journal of Organic Chemistry, 3443-3450 (2014) (Non-patent Literature 3)]. $^1$H NMR (400 MHz, DMSO-d$_6$): δ=0.90 (s, 3H), 0.93 (s, 3H), 1.17-1.25 (m, 1H), 1.27 (s, 3H), 1.35 (d, J=7.3 Hz, 3H), 1.38-1.80 (m, 8H), 2.08-2.14 (m, 1H), 2.46 (br s, 1H), 3.10-3.19 (m, 1H), 7.43 (s, 1H), 10.40 (s, 1H) ppm. $^{13}$C NMR (100 MHz, DMSO-d$_6$): δ=18.3, 19.9, 21.6, 21.7, 23.5, 32.9, 33.0, 34.4, 34.7, 38.9, 39.7, 41.3, 53.4, 107.9, 114.9, 119.2, 124.4, 140.8, 145.8, 147.2, 155.2, 189.7 ppm. IR (neat): ν=2929, 2867, 2359, 2341, 1684, 1623, 1576, 1521, 1418, 1297, 1157, 1094, 1004, 945, 806, 757, 721, 644, 605 cm$^{-1}$. HRMS (EI): calcd for C$_{22}$H$_{28}$O$_4$ [M]$^+$ 356.1988; found 356.1994.

[Production Example 6] Synthesis of LG-2

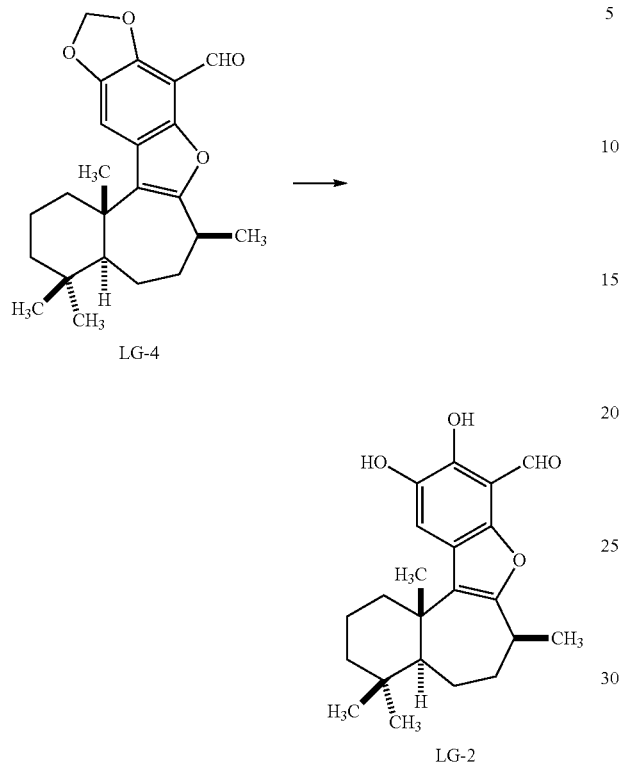

The synthesis of a compound (LG-2) was performed in the same manner as the synthesis of LG-1 except that the compound (LG-4) was used in place of the compound (LG-3) as a starting material.

$^1$H NMR (400 MHz, CDCl$_3$): δ=0.95 (s, 3H), 0.98 (s, 3H), 1.19-1.27 (m, 2H), 1.36 (s, 3H), 1.37 (s, 3H), 1.42-1.93 (m, 8H), 2.50 (dd, J=1.5, 13.4 Hz, 1H), 3.26-3.32 (m, 1H), 5.35 (s, 1H), 7.49 (s, 1H), 10.44 (s, 1H), 11.22 (s, 1H) ppm. $^{13}$C NMR (100 MHz, CDCl$_3$): δ=18.7, 18.8, 20.4, 22.3, 22.7, 31.1, 33.7, 34.5, 35.9, 39.1, 40.2, 42.0, 50.3, 106.4, 115.5, 120.4, 124.9, 139.5, 145.3, 147.7, 155.3, 192.4 ppm. IR (neat): ν=3445, 2926, 2864, 2329, 1868, 1771, 1733, 1716, 1698, 1684, 1653, 1558, 1541, 11521, 507, 1456, 1376, 1330, 1300, 1187, 1146, 1119, 992, 875, 756, 736, 618, 607 cm$^{-1}$. HRMS (EI): calcd for C$_{24}$H$_{34}$O$_4$ [M]$^+$ 356.20; found: 356.1977.

[Production Example 7] Synthesis of SD-3

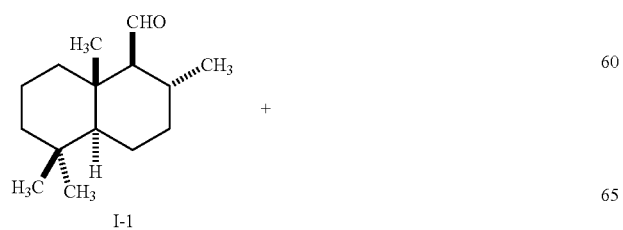

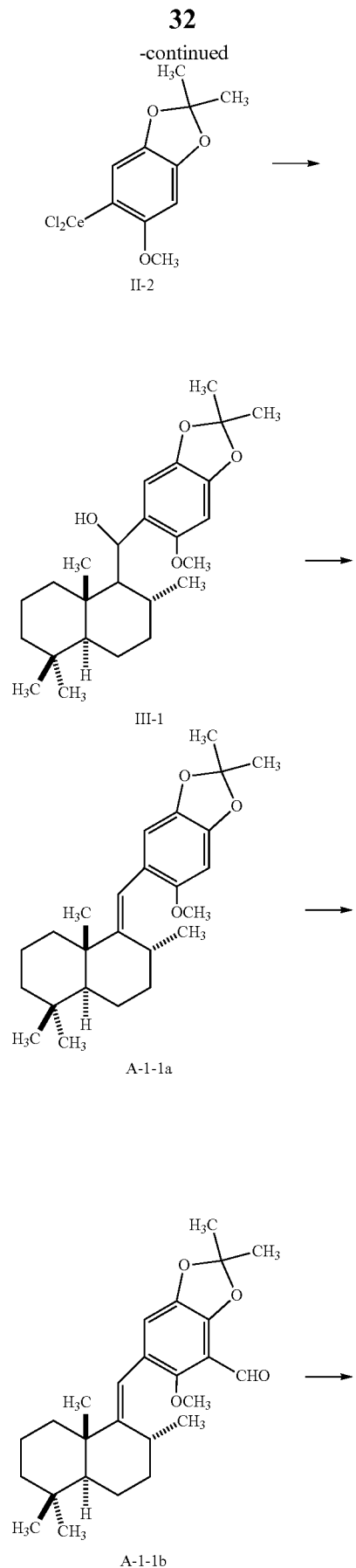

-continued

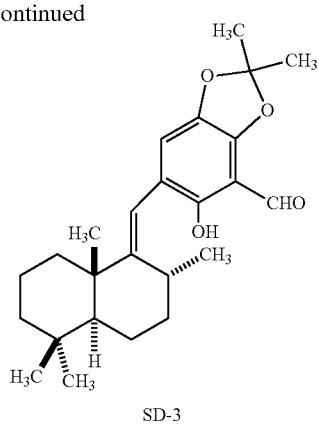

SD-3

A solution (2 mL) of (1S,2R,4aS,8aS)-2,5,5,8a-tetramethyldecahydronaphthalene-1-carbaldehyde (I-1) (312 mg, 1.4 mmol) in tetrahydrofuran was added to a solution (12 mL) of an arylcerium reagent (II-2) (1.3 g, 5.0 mmol) in tetrahydrofuran at −78° C., and the mixture was stirred at the same temperature for 1 hour. A saturated aqueous solution of ammonium chloride (20 mL) was added to the reaction mixture, followed by extraction with ethyl acetate (2×100 mL). The extract was washed with brine and dried over magnesium sulfate, and then the solvent was removed by evaporation under reduced pressure. The resultant residue was purified by silica gel column chromatography (hexane:ethyl acetate 50:1) to afford an adduct (III-1) (548 mg, 97%) as a colorless amorphous solid. $^1$H NMR (400 MHz, CDCl$_3$): δ=0.84 (d, J=7.8 Hz, 3H), 0.85 (s, 3H), 0.86 (s, 3H), 0.90 (d, J=2.4 Hz, 1H), 0.98-1.08 (m, 2H), 1.09 (s, 3H), 1.11-1.19 (m, 1H), 1.25-1.46 (m, 4H), 1.55-1.61 (m, 2H), 1.64 (s, 3H), 1.66 (s, 3H), 1.74-1.79 (m, 1H), 1.91-1.99 (m, 2H), 2.48 (d, J=4.4 Hz, 1H), 3.77 (s, 3H), 5.26 (d, J=4.4 Hz, 1H), 6.40 (s, 1H), 6.91 (s, 1H) ppm. $^{13}$C NMR (100 MHz, CDCl$_3$): δ=15.0, 19.0, 22.0 (2C), 23.4, 25.6 (2C), 28.7, 33.5, 33.8, 37.8, 39.1, 39.4, 42.3, 55.1, 56.0, 59.3, 67.2, 94.3, 107.7, 117.8, 126.9, 140.7, 146.0, 150.9 ppm. IR (neat): ν=3461, 2989, 2933, 2868, 2843, 1627, 1493, 1464, 1418, 1385, 1375, 1345, 1298, 1268, 1244, 1216, 1191, 1156, 1124, 1081, 1065, 1009, 980, 958, 934, 886, 844, 820, 802, 788, 758, 667 cm$^{-1}$. HRMS (EI): calcd. for C$_{25}$H$_{38}$O$_4$ [M]$^+$ 402.2770; found 402.2773.

Magnesium bromide (432 mg, 2.4 mmol) was added to a mixed solution of the adduct (III-1) (189 mg, 0.47 mmol) in dichloromethane (4 mL) and acetic anhydride (1 mL) under stirring at room temperature. After having been stirred for 30 minutes, the reaction mixture was diluted with dichloromethane (20 mL). The organic layer was sequentially washed with water, a saturated aqueous solution of sodium bicarbonate, and brine, and dried over magnesium sulfate, and then the solvent was removed by evaporation under reduced pressure. The resultant residue was purified by silica gel column chromatography (hexane:ethyl acetate 100:1) to afford an olefin compound (A-1-1a) (148 mg, 82%) as a colorless oil. $^1$H NMR (400 MHz, CDCl$_3$): δ=0.87 (s, 3H), 0.90 (s, 3H), 0.91 (d, J=6.8 Hz, 3H), 1.16 (s, 3H), 1.18-1.26 (m, 2H), 1.32-1.57 (m, 6H), 1.66 (s, 3H), 1.65 (s, 3H), 1.68-1.79 (m, 2H), 1.85 (d, J=11.2 Hz, 1H), 2.66-2.70 (m, 1H), 3.71 (s, 3H), 6.14 (s, 1H), 6.39 (s, 1H), 6.52 (s, 1H) ppm. $^{13}$C NMR (100 MHz, CDCl$_3$): δ=19.6, 19.9, 21.7, 22.1, 23.1, 25.7 (20), 31.7, 32.2, 33.2, 34.0, 39.7, 40.8, 42.4, 49.5, 56.9, 95.2, 110.0, 115.4, 117.6, 121.3, 140.6, 146.0, 151.6, 156.9 ppm. IR (neat): ν=2989, 2932, 2869, 2844, 1615, 1492, 1463, 1416, 1385, 1374, 1349, 1268, 1247, 1216, 1190, 1158, 1067, 1013, 980, 888, 842, 828, 818, 789, 759 cm$^{-1}$. HRMS (EI): calcd. for C$_{25}$H$_{36}$O$_3$[M]$^+$ 384.2665; found 384.2663.

Under an argon atmosphere, n-butyllithium (2.6 M hexane solution, 0.43 mL, 1.2 mmol) was added dropwise to a solution (4 mL) of the olefin compound (A-1-1a) (148 mg, 0.49 mmol) in tetrahydrofuran under stirring at −20° C. After 30 minutes of stirring, N,N-dimethylformamide (0.29 mL, 3.85 mmol) was added dropwise at the same temperature, and the mixture was further stirred for 30 minutes. A saturated aqueous solution of ammonium chloride (2 mL) was added to the reaction mixture, followed by extraction with diethyl ether (2×25 mL). The extract was washed with brine and dried over magnesium sulfate, and then the solvent was removed by evaporation under reduced pressure. The resultant residue was purified by silica gel column chromatography (hexane:ethyl acetate 20:1) to afford an aldehyde compound (A-1-1b) (151 mg, 95%) as a colorless amorphous solid.

$^1$H NMR (400 MHz, CDCl$_3$): δ=0.88 (s, 3H), 0.92 (s, 3H), 0.93 (d, J=6.8 Hz, 3H), 1.18 (s, 3H), 1.15-1.23 (m, 1H), 1.31 (dd, J=4.9, 12.2 Hz, 1H) 1.36-1.59 (m, 6H), 1.73 (s, 3H), 1.74 (s, 3H), 1.65-1.81 (m, 2H), 1.85 (d, J=12.2 Hz, 1H), 2.66-2.72 (m, 1H), 3.75 (s, 3H), 6.17 (s, 1H), 6.72 (s, 1H), 10.27 (s, 1H) ppm. $^{13}$C NMR (100 MHz, CDCl$_3$): δ=19.5, 20.1, 21.7, 22.1, 22.8, 25.9 (2C), 32.1, 32.5, 33.2, 34.0, 39.7, 41.0, 42.4, 49.9, 62.2, 113.9, 114.0, 115.4, 120.6, 125.8, 143.8, 146.3, 152.9, 158.5, 188.8 ppm. IR (neat): ν=2931, 2868, 1689, 1616, 1599, 1469, 1386, 1282, 1225, 1202, 1088, 1048, 1004, 978, 883, 836, 790, 756, 712 cm$^{-1}$. HRMS (EI): calcd. for C$_{26}$H$_{36}$O$_4$ [M]$^+$ 412.2613; found 412.2604.

Under an argon atmosphere, n-butyllithium (2.6 M hexane solution, 0.69 mL, 1.8 mmol) was added dropwise to a solution (5 mL) of n-butanethiol (0.20 mL, 1.8 mmol) in hexamethylphosphoric triamide under stirring at room temperature. After 15 minutes, the reaction mixture was cooled to 0° C., and a solution (4 mL) of the aldehyde compound (A-1-1b) (148 mg, 0.49 mmol) in tetrahydrofuran was added. The reaction mixture was increased in temperature to room temperature, and further stirred for 1 hour. A saturated aqueous solution of ammonium chloride (3 mL) was added to the reaction mixture, followed by extraction with diethyl ether (2×25 mL). The extract was washed with brine and dried over magnesium sulfate, and then the solvent was removed by evaporation under reduced pressure. The resultant residue was purified by silica gel column chromatography (hexane:ethyl acetate 100:1) to afford a phenol derivative (SD-3) (133 mg, 91%) as a yellowish orange solid.

$^1$H NMR (400 MHz, CDCl$_3$): δ=0.87 (s, 3H), 0.90 (s, 3H), 0.91 (d, J=7.3 Hz, 3H), 1.17 (s, 3H), 1.19-1.23 (m, 1H), 1.30-1.57 (m, 7H), 1.71 (s, 3H), 1.71 (s, 3H), 1.63-1.79 (m, 2H), 1.85 (d, J=12.7 Hz, 1H), 2.64-2.70 (m, 1H), 6.09 (s, 1H), 6.76 (s, 1H), 10.08 (s, 1H), 10.59 (s, 1H) ppm. $^{13}$C NMR (100 MHz, CDCl$_3$): δ=19.5, 20.0, 21.7, 22.1, 23.1, 25.7 (2C), 32.0, 32.5, 33.2, 34.0, 39.6, 41.0, 42.4, 49.8, 106.5, 113.4, 118.1, 119.1, 120.4, 139.4, 148.4, 151.5, 158.9, 191.5 ppm. IR (KBr): ν=3435, 2930, 2869, 1655, 1639, 1610, 1475, 1467, 1459, 1397, 1377, 1300, 1253, 1221, 1200, 1163, 1162, 1020, 1002, 701 cm$^{-1}$. HRMS (EI): calcd. for C$_{25}$H$_{34}$O$_4$ [M]$^+$398.2457; found 398.2464.

[Production Example 8] Synthesis of SD-1

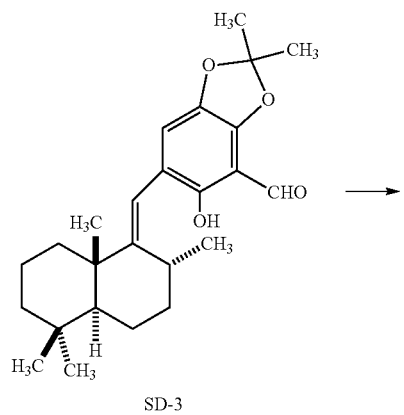

SD-3

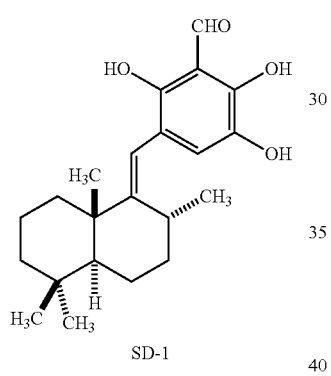

SD-1

Under an argon atmosphere, boron trichloride (1.0 M dichloromethane solution, 0.62 mL, 0.62 mmol) was added dropwise to a solution (2 mL) of SD-3 (49.7 mg, 0.13 mmol) in dichloromethane under stirring at −40° C. After 30 minutes of stirring, a saturated aqueous solution of sodium bicarbonate (2 mL) was added to the reaction mixture, followed by extraction with dichloromethane (2×25 mL). The extract was washed with brine and dried over magnesium sulfate, and then the solvent was removed by evaporation under reduced pressure. The resultant residue was purified by gel filtration chromatography (Sephadex LH-20, methanol) to afford siphonodictyal B (SD-1) (33.4 mg, 75%) as a yellow solid.

$^1$H NMR (400 MHz, CDCl$_3$): δ=0.75 (d, J=6.8 Hz, 3H), 0.86 (s, 3H), 0.89 (s, 3H), 1.16 (s, 3H), 1.11-1.30 (m, 3H), 1.41-1.82 (m, 8H), 2.52-2.61 (m, 1H), 5.12 (br. s, 1H), 5.41 (br. s, 1H), 5.90 (s, 1H), 6.83 (s, 1H), 10.29 (s, 1H), 11.45 (br. s, 1H) ppm. $^{13}$C NMR (100 MHz, CDCl$_3$): δ=19.4, 21.1, 21.2, 21.7, 22.6, 33.2, 33.9, 34.1, 34.7, 39.3, 41.9, 42.3, 52.3, 109.1, 109.5, 116.9, 123.7, 136.9, 147.6, 148.5, 165.8, 194.5 ppm; IR (KBr): ν=3383, 2929, 2870, 1644, 1458, 1389, 1375, 1306, 1270, 938, 757 cm$^{-1}$. HRMS (EI): calcd. for C$_{22}$H$_{30}$O$_4$ [M]$^+$ 358.2144; found 358.2159.

[Production Example 9] Synthesis of SD-2

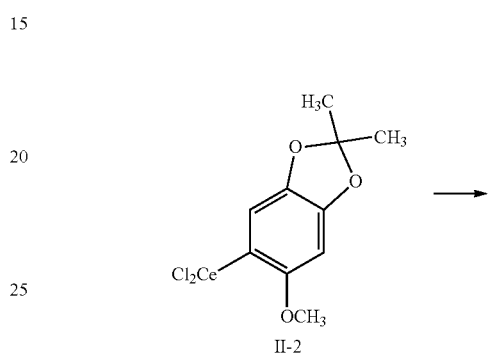

I-2

II-2

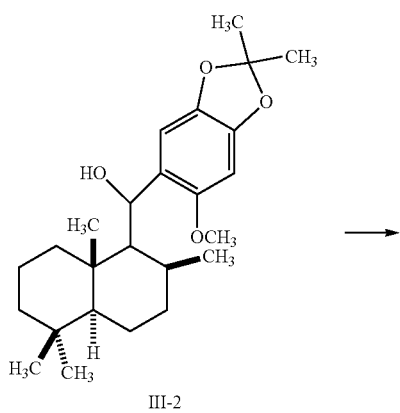

III-2

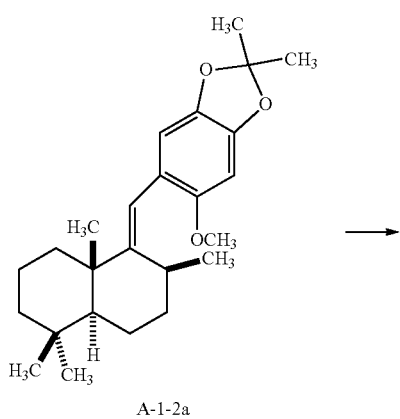

A-1-2a

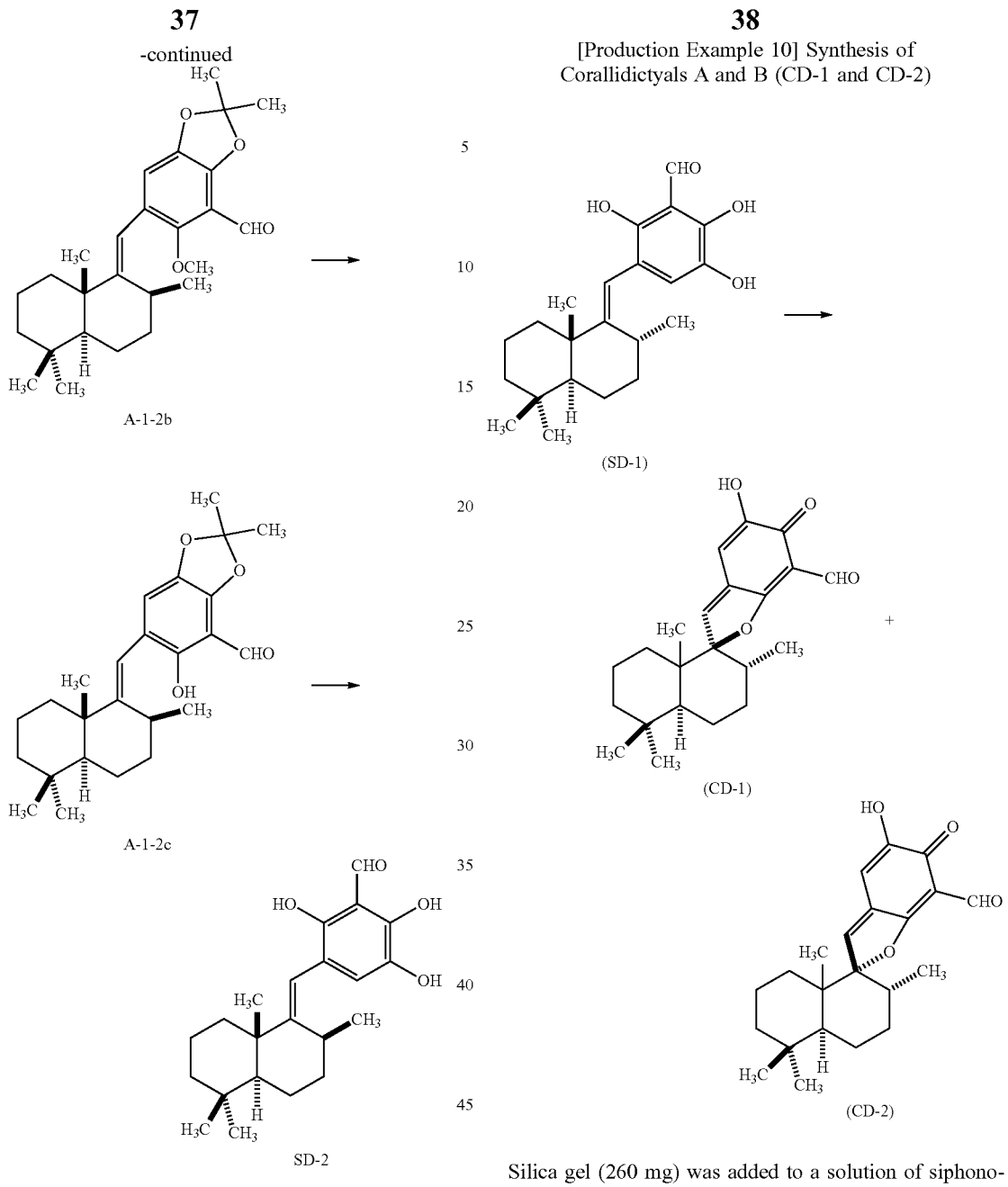

[Production Example 10] Synthesis of Corallidictyals A and B (CD-1 and CD-2)

The synthesis of SD-2 (8-epi-siphonodictyal B) was performed in the same manner as [Example 7] Synthesis of SD-3 and [Example 8] Synthesis of SD-1 except that a (1S,2S,4aS,8aS)-isomer (1-2) was used in place of (1S,2R,4aS,8aS)-2,5,5,8a-tetramethyldecahydronaphthalene-1-carbaldehyde (I-1) as a starting material.

$^1$H NMR (400 MHz, CDCl$_3$): δ=0.88 (s, 6H), 1.93-1.96 (m, 1H), 1.09 (d, J=7.3 Hz, 3H), 1.20 (s, 3H), 1.14-1.22 (m, 1H), 1.40-1.76 (m, 8H), 1.83 (d, J=12.6 Hz, 1H), 2.66-2.73 (m, 1H), 5.08 (br. s, 1H), 5.51 (br. s, 1H), 5.83 (s, 1H), 6.81 (s, 1H), 10.31 (s, 1H), 11.35 (br. s, 1H) ppm. $^{13}$C NMR (100 MHz, CDCl$_3$): δ=17.7, 18.8, 21.8, 22.5, 22.7, 31.6, 33.4, 34.0, 34.1, 38.0, 41.3, 42.0, 55.0, 109.4, 110.7, 115.7, 123.7, 137.0, 147.6, 148.9, 165.6, 194.6 ppm. IR (KBr): ν=3398, 2921, 2869, 1655, 1638, 1609, 1459, 1439, 1399, 1388, 1254, 1204, 1018, 947 cm$^{-1}$. HRMS (EI): calcd. for C$_{22}$H$_{30}$O$_4$ [M]$^+$ 358.2144; found 358.2146.

Silica gel (260 mg) was added to a solution of siphonodictyal B (SD-1) (13.0 mg, 36 μmol) in ethyl acetate (3.6 mL) under stirring at room temperature, and the mixture was stirred at the same temperature for 20 hours. The solvent of the reaction mixture was removed by evaporation under reduced pressure, and the resultant residue was purified by silica gel column chromatography (hexane:ethyl acetate 3:1) to afford a mixture of corallidictyal A (CD-1) and corallidictyal B (CD-2) (CD-1/CD-2=1:2.7) (10.1 mg, 78%) as a yellow oil. This mixture was difficult to separate.

IR (neat): ν=3325, 3078, 2932, 2870, 1692, 1643, 1619, 1598, 1583, 1566, 1458, 1390, 1309, 1271, 1232, 1199, 1178, 1122, 1070, 1010, 982, 939, 910, 876, 794, 755, 722 cm$^{-1}$. HRMS (EI) calcd for C$_{22}$H$_{28}$O$_4$ [M]$^+$356.1988; found 356.1992. Corallidictyal A (CD-1)

$^1$H NMR (400 Hz, CDCl$_3$): δ=0.54 (d, J=6.6 Hz, 3H), 0.90 (s, 3H), 0.93 (s, 3H), 1.35 (s, 3H), 0.77-1.84 (m, 10H), 1.98-2.03 (m, 1H), 2.60-2.66 (m, 1H), 6.48 (s, 1H), 7.42 (br. s, 1H), 7.51 (s, 1H), 10.27 (s, 1H) ppm. $^{13}$C NMR (100 Hz, CDCl$_3$): δ=15.5, 16.5, 18.25, 21.52, 21.88, 33.5, 33.6, 33.7, 33.9, 35.6, 41.7, 44.9, 52.4, 98.4, 107.7, 113.1, 131.8, 147.7, 150.3, 175.8, 180.3, 186.6 ppm.

Corallidictyal B(CD-2)

$^1$H NMR (400 Hz, CDCl$_3$): δ=0.55 (d, J=6.6 Hz, 3H), 0.87 (s, 3H), 0.95 (s, 3H), 1.27 (s, 3H), 0.77-1.84 (m, 11H), 2.39-2.48 (m, 1H), 6.43 (s, 1H), 7.25 (s, 1H), 7.43 (br. s, 1H), 10.30 (s, 1H) ppm. $^{13}$C NMR (100 Hz, CDCl$_3$): δ=15.6, 18.21, 19.4, 21.49, 21.90, 32.0, 32.9, 33.3, 33.8, 34.2, 41.2, 44.0, 47.4, 98.2, 117.8, 111.2, 130.9, 149.7, 150.4, 177.0, 180.0, 186.2 ppm.

[Production Example 11] Synthesis of 8-epi-Corallidictyal B

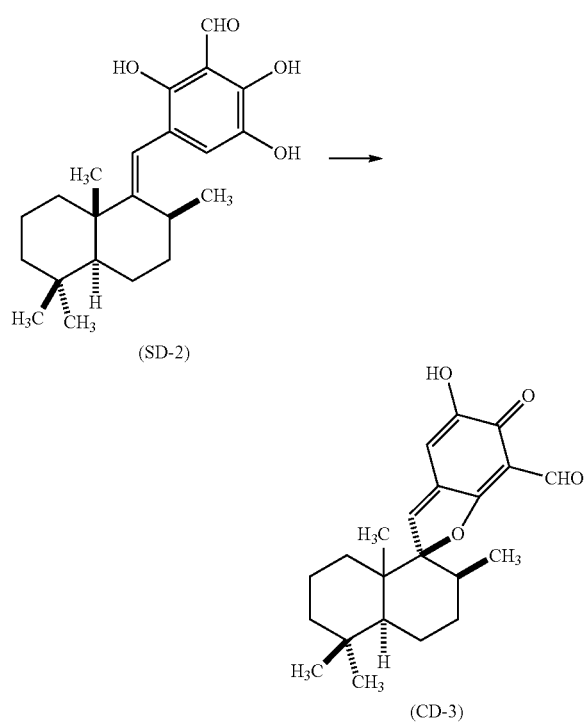

Silica gel (216 mg) was added to a solution (3 mL) of 8-epi-siphonodictyal B (SD-2) (10.8 mg, 30 μmol) in ethyl acetate under stirring at room temperature, and the mixture was stirred at the same temperature for 20 hours. The solvent of the reaction mixture was removed by evaporation under reduced pressure, and the resultant residue was purified by silica gel column chromatography (hexane:ethyl acetate 3:1) to afford 8-epi-corallidictyal B (CD-3) (9.3 mg, 87%) as a yellow oil.

$^1$H NMR (400 Hz, CDCl$_3$): δ=0.88 (s, 3H), 0.97 (s, 3H), 0.83-1.03 (m, 1H), 1.31 (s, 3H), 1.14-1.39 (m, 7H), 1.50-1.81 (m, 6H), 2.15-2.24 (m, 1H), 6.43 (s, 1H), 7.44 (s, 1H), 7.53 (s, 1H), 10.28 (s, 1H) ppm. $^{13}$C NMR (100 Hz, CDCl$_3$): δ=17.1, 17.6, 19.6, 19.9, 21.7, 30.9, 32.7, 33.3, 33.7, 40.5, 41.3, 43.7, 48.6, 98.4, 108.2, 111.8, 130.8, 149.8, 150.4, 175.7, 179.9, 186.2 ppm. IR (neat): ν=3323, 2938, 1692, 1619, 1598, 1583, 1456, 1393, 1313, 1271, 1183, 1141, 1004, 940, 794, 755, 722, 655 cm$^{-1}$. HRMS (EI) calcd for C$_{22}$H$_{28}$O$_4$ [M]$^+$ 356.1988; found 356.1997.

Example 1 Assessment of PI3Kα Inhibitory Activity

The compounds obtained in Production Examples described above were each measured for its IC50 value for PIK3α (PIK3CA/PIK3R1) by mobility shift assay. The mobility shift assay is a method involving separating and quantifying a substrate and a phosphorylated substrate on the basis of mobility in a capillary. Each compound was mixed at various concentrations with an assay buffer (20 mM HEPES, 2 mM DTT, 25 μM sodium cholate, 75 mM NaCl, 20 μM cantharidine) together with 21 nM PI3K, 1,000 nM phosphatidyl inositol, 50 μM ATP, and 5 mM MgCl, and the mixture was subjected to a reaction at room temperature for 5 hours, followed by the mobility shift assay. The test was repeated twice. The enzymatic reaction was assessed on the basis of a product ratio (P/(P+S)) calculated from the height of a substrate peptide peak (S) and the height of a phosphorylated peptide peak (P). An inhibition rate was calculated from a signal obtained when each compound was added, with the average signal of a control containing all reaction components being defined as 0% inhibition and the average signal of a background (no enzyme added) being defined as 100% inhibition. The results are shown in FIG. 1.

As shown in FIG. 1, all the compounds were found to have inhibitory activity against PI3Kα. In a previous report (J Anderson et. al. Organic Letters, 2006, vol. 8, No 2, 321-324), the IC50 of LG-1 is 0.1 μM, but the measurement of the IC50 value is based on a fluorescence polarization method completely different from the test performed herein, and hence the difference in assay method may be involved.

Example 2 Investigation of Kinase Inhibition Profile

Figure 2:
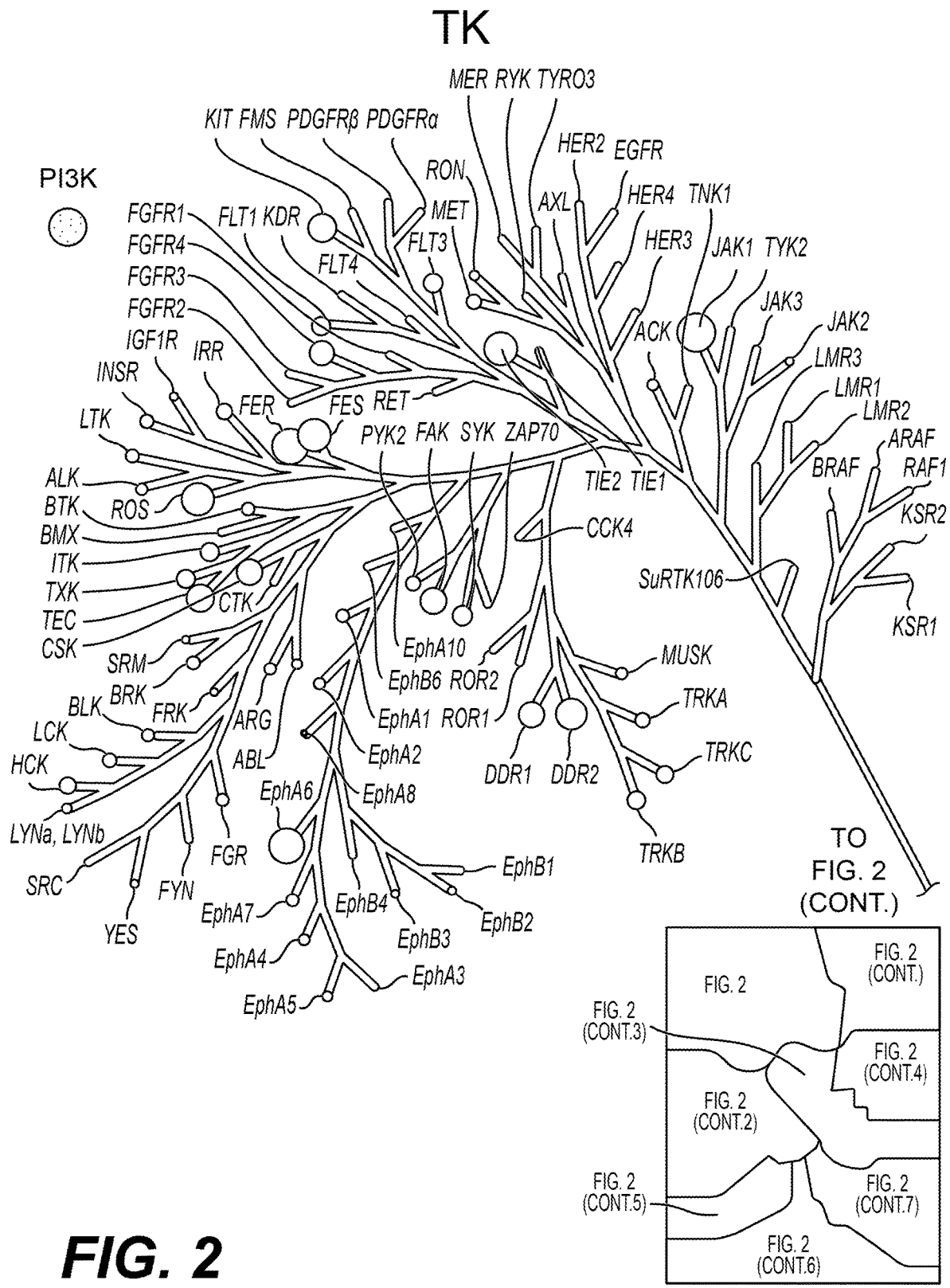
FIG. 2 is a protein kinase phylogenetic tree on which inhibitory activity (% inhibition) against each kinase assessed in Example 2 is represented by the size of a bubble.
Figure 2:
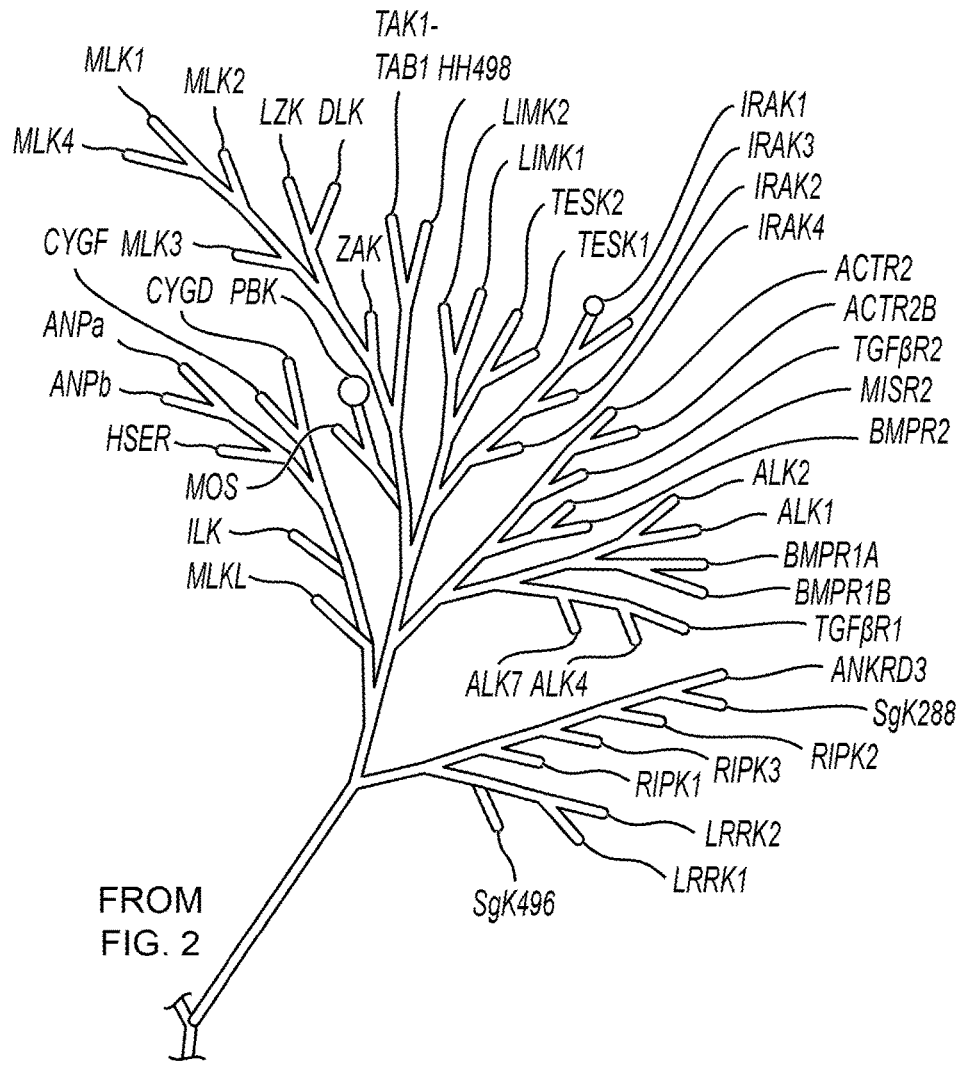
Figure 2:
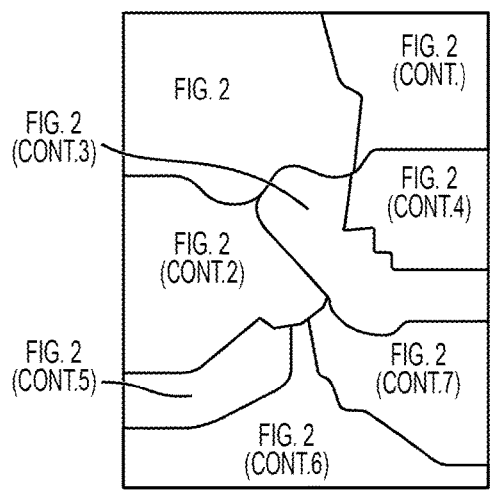
Figure 2:
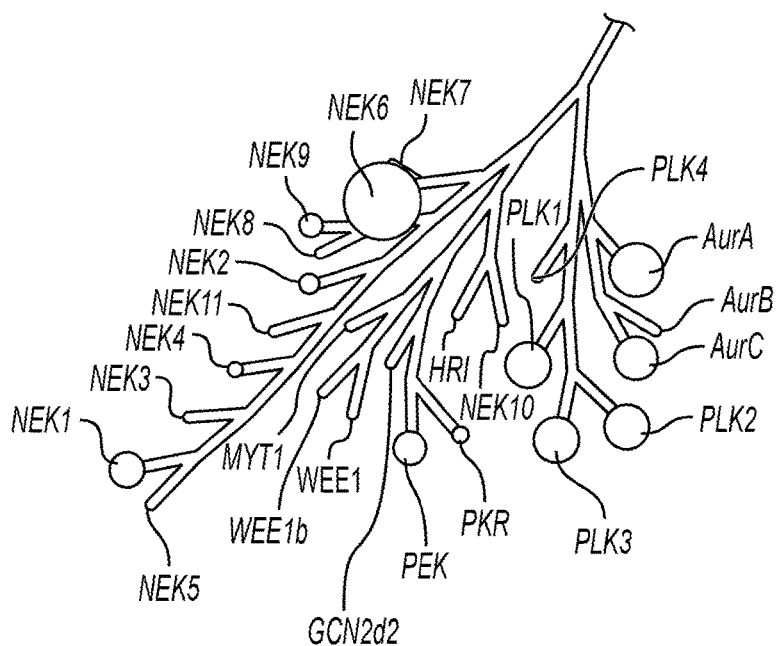
Figure 2:
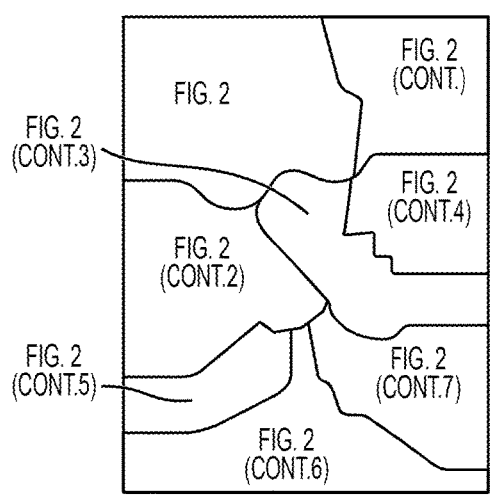
Figure 2:
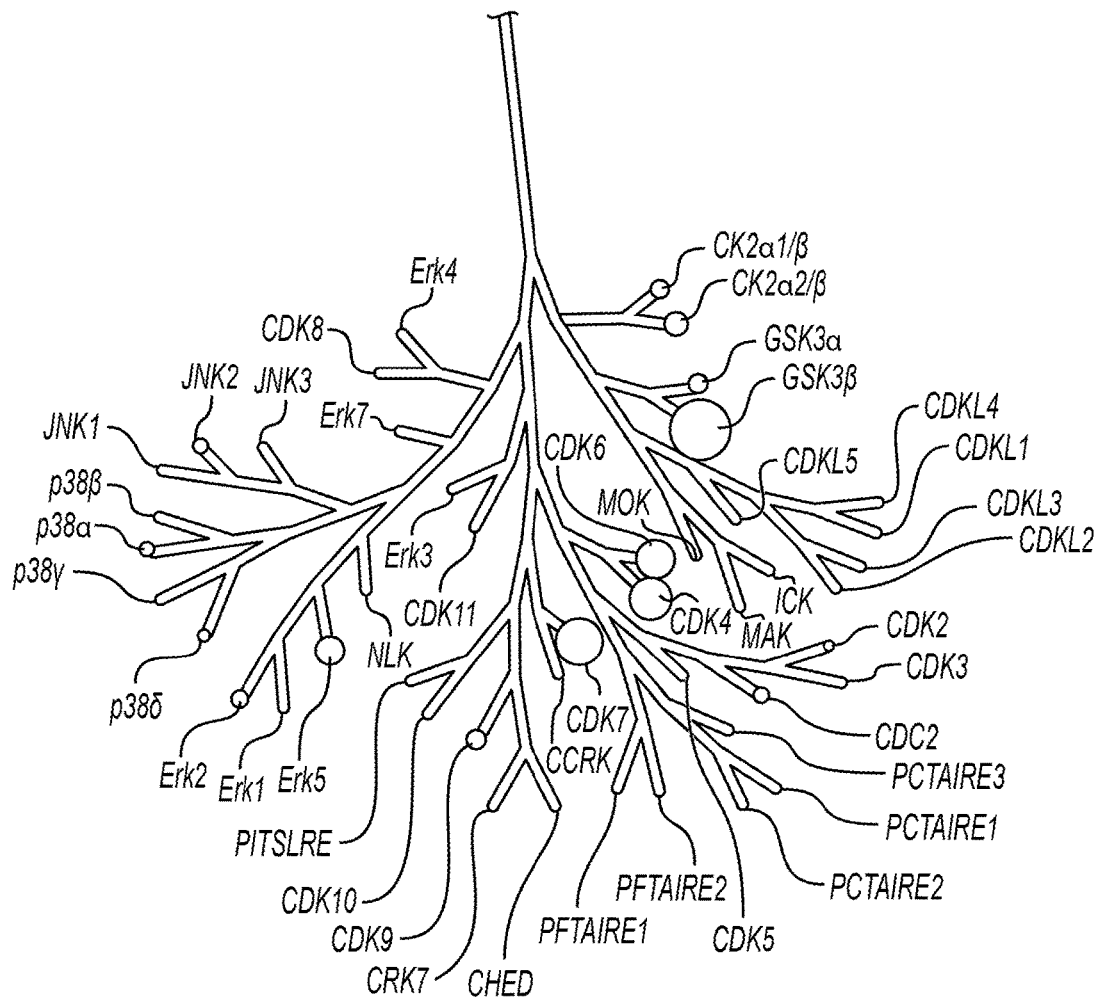
Figure 2:
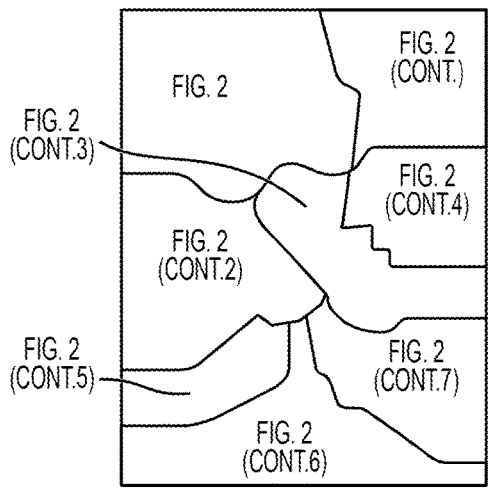
Figure 2:
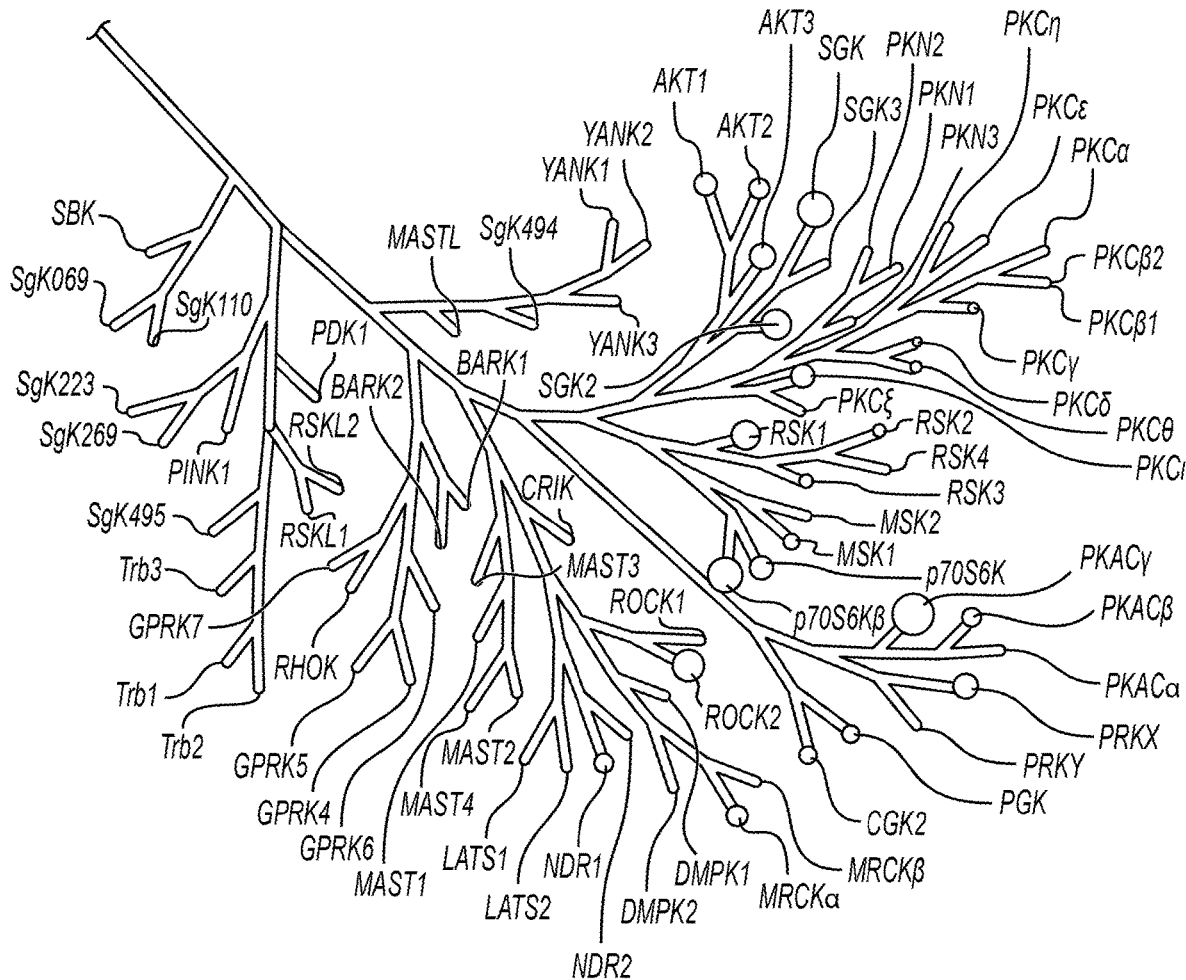
Figure 2:
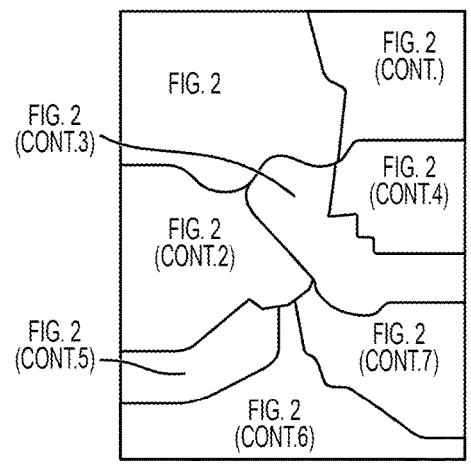

LG-1 (liphgal) at 10 μM was assessed for its inhibitory activity against 313 kinds of kinases by mobility shift assay or IMAP Assay™ (Carna Biosciences). Specifically, the assessment was performed by the IMAP Assay™ (Carna Biosciences) for SPRK1, PLK2, PKR, PKN1, PEK, IRAK1, and EKKα among the 313 kinds of kinases, and the assessment was performed by the mobility shift assay for all the other kinases. Inhibitory activity (% inhibition) against each kinase is represented by the size of a bubble on a protein kinase phylogenetic tree of FIG. 2. The size of a bubble represents inhibitory activity against each kinase, and a larger bubble indicates more potent inhibitory activity. PI3Kα is a lipid kinase and is not included in the protein kinase phylogenetic tree, and hence its bubble is separately shown. Inhibitory activity was found against a plurality of kinases in addition to PI3Kα, revealing that liphagal was a multi-targeted kinase inhibitor.

In addition, specific numerical values for the inhibitory activity of liphagal at 10 μM against the 313 kinds of kinases are shown in Table 1-1 below. In Table 1-2, kinases each showing an inhibition rate of 50% or more (kinases for each of which the IC50 value of LG-1 is predicted to be 10 μM or less) are selectively shown. Potent inhibitory activity was found against a plurality of kinases including kinases associated with the cell cycle, such as CDK7, CDK6, and CDK4. In addition, potent inhibitory activity against PIM2 was also found

TABLE 1-1

| Tested Kinase | % Inhibition |
|---|---|
| CDK7/CycHMAT1 | 85.8 |
| TSSK3 | 85.6 |
| PIK3CA/PIK3R1 | 83.4 |
| MST 4 | 80.3 |
| COK6/CycD3 | 72.7 |

TABLE 1-1-continued

| Tested Kinase | % Inhibition |
|---|---|
| NEK6 | 65.4 |
| PIM2 | 63.5 |
| CDK4/CycD3 | 63.4 |
| MAP3K4_Cascade | 62.9 |
| MST3 | 62.7 |
| DDR1 | 60.5 |
| SPHK1 | 59.8 |
| CaMK1δ | 57.7 |
| AurA | 53.9 |
| BRK | 52.5 |
| CaMK4 | 51.4 |
| PIM 1 | 50.3 |
| MELK | 49.2 |
| MAP3K3_Cascade | 48.8 |
| PDHK2 | 47.2 |
| AMFKα2/β1/γ1 | 44.1 |
| FER | 42.8 |
| DDR2 | 42.5 |
| CDK3/CycE1 | 40.1 |
| DYRK3 | 39.2 |
| MAP3K5_Cascade | 38.0 |
| CK1ε | 37.7 |
| TRKA | 36.4 |
| AurC | 36.3 |
| IKKα | 34.4 |
| RSK1 | 34.3 |
| SIK | 33.7 |
| CDC2/CycB1 | 33.7 |
| PLK1 | 31.3 |
| PLK3 | 31.1 |
| CLK1 | 30.1 |
| MOS_Cascade | 29.5 |
| BLK | 29.4 |
| PDGFRα(T674I) | 29.2 |
| PIM 3 | 28.9 |
| SRPK1 | 28.2 |
| NEK9 | 27.3 |
| HPK2 | 27.0 |
| CHK2 | 26.5 |
| MAP3K1_Cascade | 26.4 |
| p70S6Kβ | 26.4 |
| CDC7/ASK | 26.2 |
| HPK1 | 26.1 |
| CaMK1α | 25.7 |
| MAP2K3_Cascade | 25.6 |
| GSK3β | 25.3 |
| TAOK2 | 24.5 |
| FAK | 24.5 |
| NEK7 | 24.4 |
| MST 1 | 24.3 |
| FES | 23.4 |
| TXK | 23.1 |
| GSK3α | 23.1 |
| IRR | 23.1 |
| EPHA6 | 23.0 |
| EEF2K | 22.4 |
| KIT(V654A) | 22.3 |
| DYRK1B | 21.8 |
| PHKG1 | 21.7 |
| PYK2 | 21.6 |
| TSSK2 | 21.0 |
| WNK2 | 20.7 |
| CKIα | 20.5 |
| HPK3 | 20.5 |
| PRKX | 20.0 |
| MAP2K6_Cascade | 19.9 |
| AMPKα1/β1/γ1 | 19.9 |
| PLK2 | 19.7 |
| MLK3_Cascade | 19.5 |
| BRAF(V600E)_Cascade | 19.5 |
| KIT(D816E) | 19.4 |
| SRM | 19.0 |
| WNK3 | 19.0 |
| DYRK2 | 18.9 |
| CDK9/CycT1 | 18.8 |
| PKACγ | 18.7 |
| HPK4 | 18.2 |
| KIT(V560G) | 17.9 |
| HER4 | 17.9 |
| CDK5/p25 | 17.8 |
| SPHK2 | 17.4 |
| PASK | 17.4 |
| WNK1 | 17.3 |
| SYK | 17.0 |
| MAP3K2_Cascade | 16.8 |
| MLK1_Cascade | 16.3 |
| MRCKα | 16.0 |
| p70S6K | 15.9 |
| TRKB | 15.8 |
| LOK | 15.8 |
| RAF1_Cascade | 15.3 |
| BRAF_Cascade | 15.0 |
| JAK1 | 14.9 |
| RET(G691S) | 14.8 |
| COT_Cascade | 14.7 |
| RSK2 | 14.5 |
| INSR | 14.1 |
| DCAMKL2 | 14.0 |
| DLK_Cascade | 13.9 |
| NEK1 | 13.9 |
| PKACβ | 13.9 |
| TAK1-TAB1_Cascade | 13.9 |
| PKR | 13.8 |
| PEK | 13.2 |
| KIT(D816V) | 13.0 |
| PBK | 13.0 |
| FM8 | 12.5 |
| PAK2 | 12.4 |
| SGK | 12.4 |
| PKCι | 12.3 |
| AurA/TPX2 | 12.2 |
| AurB | 12.1 |
| TIE2 | 11.7 |
| TRKC | 11.3 |
| LCK | 11.0 |
| JNK2 | 10.7 |
| RET | 10.6 |
| DYRK1A | 10.5 |
| SLK | 10.5 |
| FTI1 | 10.4 |
| BTK | 10.3 |
| CDK2/CycA2 | 10.3 |
| RET(Y791F) | 9.9 |
| SRPK2 | 9.7 |
| FGR | 9.3 |
| BRSK2 | 9.3 |
| SGK2 | 9.3 |
| M88K1 | 9.3 |
| BRSK1 | 9.2 |
| p38B | 9.1 |
| MAP2K4 Cascade | 9.1 |
| ALK | 9.0 |
| CK2α2/β | 9.0 |
| IGF1R | 8.7 |
| NEK4 | 8.7 |
| EPHA7 | 8.7 |
| ROS | 8.6 |
| ACK | 8.4 |
| MLK2_Cascade | 8.3 |
| PDGFRα | 8.2 |
| RSK3 | 8.1 |
| FGFR4(V550L) | 7.8 |
| RON | 7.8 |
| CaMK2δ | 7.7 |
| LYNa | 7.6 |
| MST2 | 7.6 |
| FGFR4 | 7.5 |
| PDHK4 | 7.4 |
| RSK4 | 7.4 |
| CGK2 | 7.3 |
| CSK | 7.2 |
| PDGFRα(V561D) | 7.1 |
| CDK2/CycE1 | 6.9 |
| BMX | 6.5 |
| KIT(D816Y) | 6.2 |
| AKT2 | 6.2 |

TABLE 1-1-continued

| Tested Kinase | % Inhibition |
|---|---|
| Etk2 | 6.2 |
| PGK | 6.1 |
| ABL(T315I) | 6.1 |
| KIT | 6.0 |
| NuaK1 | 6.0 |
| MNK2 | 5.9 |
| RET(M918T) | 5.9 |
| CLK3 | 5.7 |
| MAP2K7_Cascade | 5.5 |
| EFHB2 | 5.4 |
| KIT(T670I) | 5.4 |
| MNK1 | 5.3 |
| PKN1 | 5.3 |
| TNK1 | 5.1 |
| MET(Y1235D) | 5.0 |
| MAP4K2 | 5.0 |
| MSK1 | 5.0 |
| HCK | 4.8 |
| MAPKAPK3 | 4.8 |
| MAPKAPK5 | 4.8 |
| PKD1 | 4.2 |
| EGFR(L858R) | 4.2 |
| TSSK1 | 4.1 |
| OK1δ | 4.1 |
| MAP2K1 Cascade | 4.1 |
| CaMK2γ | 3.8 |
| YES(T348I) | 3.7 |
| NEK2 | 3.5 |
| AKT3 | 3.3 |
| Haspin | 3.3 |
| AKT1 | 3.1 |
| FYN(isoform b) | 3.1 |
| CK1γ3 | 3.0 |
| MET(D1228H) | 2.9 |
| CK1γ1 | 2.8 |
| PKD2 | 2.8 |
| LYNb | 2.8 |
| MAPXK2 Cascade | 2.7 |
| PKD3 | 2.7 |
| MARK2 | 2.7 |
| QIK | 2.7 |
| NDR1 | 2.6 |
| EPHA2 | 2.6 |
| EGFR(d746-750/T790M) | 2.5 |
| IKKβ | 2.4 |
| FGFR4(V550E) | 2.4 |
| PKACα | 2.3 |
| NPM1-ALK | 2.3 |
| EPHA5 | 2.3 |
| FLT4 | 2.1 |
| FLT3 | 2.1 |
| RET(S891A) | 2.1 |
| MER | 2.1 |
| EPHA4 | 2.0 |
| ROCK2 | 2.0 |
| CaMK2β | 1.9 |
| DAPK1 | 1.8 |
| LTK | 1.8 |
| EPHB1 | 1.7 |
| EPHB3 | 1.7 |
| PKCδ | 1.6 |
| PDGF Ru(DB42V) | 1.5 |
| EGFR(L861Q) | 1.5 |
| Nuak2 | 1.5 |
| PHKG2 | 1.5 |
| FRK | 1.4 |
| ARG | 1.4 |
| HGK | 1.2 |
| IRAK1 | 1.2 |
| EML4-ALK | 1.1 |
| EPHA8 | 0.8 |
| YES | 0.7 |
| Erk5 | 0.6 |
| PAK1 | 0.5 |
| ROCK1 | 0.5 |
| EPHA1 | 0.5 |
| FYN(isoform a) | 0.5 |
| MAPKAPK2 | 0.5 |

TABLE 1-1-continued

| Tested Kinase | % Inhibition |
|---|---|
| ABL | 0.4 |
| ALK(C1156Y) | 0.2 |
| TNK | 0.1 |
| p38α | 0.1 |
| MNK | 0.0 |
| p38δ | −0.1 |
| MET(M125DT) | −0.2 |
| ALK(L1152InsT) | −0.2 |
| ALK(G1202R) | −0.3 |
| SGK3 | −0.5 |
| ALK(R1275Q) | −0.5 |
| CaMK2α | −0.5 |
| TRK1 | −0.5 |
| LATS2 | −0.6 |
| JAK2 | −0.7 |
| CRIK | −0.8 |
| CK2α1/β | −0.9 |
| KDR | −1.1 |
| TEC | −1.2 |
| EPHB4 | −1.2 |
| MAP2K5 Cascade | −1.3 |
| SkMLCK | −1.3 |
| MET | −1.3 |
| ALK(L1196M) | −1.5 |
| HER2 | −1.6 |
| MGC42105 | −1.7 |
| ALK(F1174L) | −1.8 |
| PKCγ | −1.9 |
| MRCKβ | −1.9 |
| EGFR(T790M) | −2.0 |
| EGFR(T790/L858R) | −2.2 |
| FGFR1 | −2.3 |
| PAK5 | −2.5 |
| RAK4 | −2.8 |
| EPHA3 | −2.8 |
| CK1γ2 | −2.8 |
| MARK3 | −2.9 |
| ABL(E265K) | −3.3 |
| PDGFRβ | −3.4 |
| MARK1 | −3.5 |
| FGFR3(K650M) | −3.6 |
| MARK4 | −3.8 |
| AXL | −4.2 |
| FGFR3 | −4.4 |
| EGFR | −4.4 |
| Erk1 | −4.4 |
| NDR2 | −4.9 |
| EGFR(α746-750) | −5.1 |
| p38γ | −5.6 |
| JNK3 | −5.8 |
| KKε | −6.3 |
| TYK2 | −6.5 |
| ITK | −6.5 |
| TYRO3 | −6.6 |
| SRC | −7.1 |
| JAK3 | −7.2 |
| PKCζ | −7.2 |
| PKCα | −8.0 |
| MUSK | −8.4 |
| FGR3(K650E) | −8.4 |
| FGFR2 | −8.4 |
| JNK1 | −10.8 |
| MSK2 | −11.7 |
| FGFR1(V561M) | −12.6 |
| PKCβ2 | −13.2 |
| PKCθ | −15.0 |
| CHK1 | −15.3 |
| PKCβ1 | −18.0 |
| PAK4 | −24.7 |
| CLK2 | −25.5 |
| PKCη | −34.3 |
| PKCε | −46.9 |
| PDK1 | −97.8 |
| PAK6 | −99.3 |

TABLE 1-2

| Tested Kinase | % Inhibition |
|---|---|
| CDK7/CycH/MAT 1 | 85.8 |
| TSSK3 | 85.6 |
| PIK3CA/PIK3R1 | 83.4 |
| MST 4 | 80.3 |
| CDK6/CycD3 | 72.7 |
| NEK6 | 65.4 |
| PIM2 | 63.5 |
| CDK4/CycD3 | 63.4 |
| MAP3K4_Cascade | 62.9 |
| MST3 | 62.7 |
| DDR1 | 60.5 |
| SPHK1 | 59.8 |
| CaMK1δ | 57.7 |
| AurA | 53.9 |
| BRK | 52.5 |
| CaMK4 | 51.4 |
| PIM1 | 50.3 |

Example 3 Inhibitory Activity Against Kinase

The compounds produced in Production Examples described above were each assessed for its inhibitory activity against CDK7, PIM2, and PI3K by mobility shift assay. The results are shown in Table 2 below. In addition, a combination showing the highest inhibitory activity against each kinase is indicated by italics.

| | IC50 (μM) | | | | | |
|---|---|---|---|---|---|---|
| Kinase | LG-1 (Liphagal) | LG-2 | LG-3 | LG-4 | SD-1 | SD-2 |
| CDK7/CycH/MAT1 | 1.27 | 9.08 | 16.3 | 191 | 13.7 | 4.24 |
| PIM2 | 5.31 | 2.81 | 18.0 | 13.8 | 6.99 | 2.79 |
| PIK3CA/PIK3RI | 4.12 | 1.72 | 4.26 | 4.43 | 2.62 | 3.26 |

As shown in Table 2 above, each of the compounds showed inhibitory activity against CDK7, PIM2, and PI3K.

Next, the compounds produced in Production Examples described above were each assessed for its inhibitory activity against CDK4 by mobility shift assay. The results are shown in Table 3 below. In addition, a combination showing the highest inhibitory activity is indicated by italics.

| | IC50 (μM) | | | | |
|---|---|---|---|---|---|
| Kinase | LG-1 (Liphagal) | LG-2 | LG-3 | SD-1 | SD-2 |
| CDK4/CycD3 | *19.9* | 125 | 47.8 | 32.9 | 22.4 |

As shown in Table 3 above, each of the compounds showed inhibitory activity against CDK7, PIM2, and PI3K.

Next, the compounds produced in Production Examples described above were each assessed for its inhibitory activity against CDK6 by mobility shift assay. The results are shown in Table 4 below. In addition, a combination showing the highest inhibitory activity is indicated by italics.

| | IC50 (μM) | | | |
|---|---|---|---|---|
| Kinase | LG-1 (Liphagal) | LG-3 | SD-1 | SD-2 |
| CDK4/CycD3 | *6.78* | 64.1 | 69.1 | 25.6 |

As shown in Table 4 above, each of the compounds showed inhibitory activity against CDK7, PIM2, and PI3K.

LG-1 tended to show potent inhibitory actions on the kinases associated with the cell cycle.

Although the inhibitory activity against each kinase varied among the analogs, all the five kinds of analogs were also shown to have inhibitory actions on the kinases associated with the cell cycle. PIM2 is a kinase reported to be involved in potential resistance to a PI3K inhibitor, and SD-2 and LG-2 showed potent inhibitory actions thereon.

Example 4

CD-3 produced in the foregoing was used as a test substance, and was measured for its IC50 value for PIK3CA/PIK3R1 by ADP-Glo™ Kinase Assay. A specific procedure is as described below.

4-1. Preparation of Test Substance Solution

The test substance was dissolved in dimethyl sulfoxide (DMSO), and further diluted with DMSO to prepare a solution having a 100-fold concentration with respect to a Lest concentration. The solution was further diluted 25-fold with an assay buffer to prepare a test substance solution. A positive control substance was similarly treated to prepare a positive control substance solution.

4-2. Kinase

TABLE 5

| Kinase | Description |
|---|---|
| PIK3CA/ PIK3R1 | Full-length human PIK3CA[1-1068(end) amino acids of accession number NP_006209.2] was co-expressed as N-terminal DYKDDDDK tagged, biotinylated protein (128 kDa) with PIK3R1[1-724(end) amino acids of accession number NP_852664.1] using baculovirus expression system. The protein was purified by using DYKDDDDK tag antibody agarose. |

4-3. Reagent and Test Method

ADP-Glo™ Kinase Assay 1) 5 μL of a test substance solution having a 4-fold concentration, 5 μL of a substrate solution having a 4-fold concentration, 5 μL of an ATP solution having a 4-fold concentration, and 5 μL of a kinase/metal solution having a 4-fold concentration, which had been prepared with an assay buffer (50 mM MOPS, 1 mM DTT, pH 7.2), were mixed in wells of a 384 well black plate made of polystyrene, and the mixture was subjected to a reaction at room temperature for 1 hour.

2) 20 μL of an ADP-Glo™ solution (Promega) was added, and the resultant mixture was subjected to a reaction at room temperature for 40 minutes or more.

3) 40 μL of Kinase Detection Reagent (Promega) was added, and the resultant mixture was subjected to a reaction at room temperature for 40 minutes or more.

4) The kinase reaction was assessed in terms of relative light unit (RLU).

4-4. Reaction Conditions

TABLE 6

| Kinase | Platform | Substrate | | ATP (MM) | | Metal | | Positive control |
|---|---|---|---|---|---|---|---|---|
| | | Name | (nM) | Km | Assay | Name | (mM) | |
| PIK3CA/ PIK3R1 | ADP-Glo | IP(4,5)P2 | 10000 | 89 | 100 | Mg | 5 | PI-103 |

4-5. Data Analysis

An inhibition rate was calculated from the average signal of each test substance test well with the average signal of a control well containing all reaction components being defined as 0% Inhibition and the average signal of a background well (no enzyme added) being defined as 100% Inhibition.

An $IC_{50}$ value was determined by approximating a plot of test substance concentration and inhibition rate to a 4-parameter logistic curve by a nonlinear least-squares method.

Figure 4:
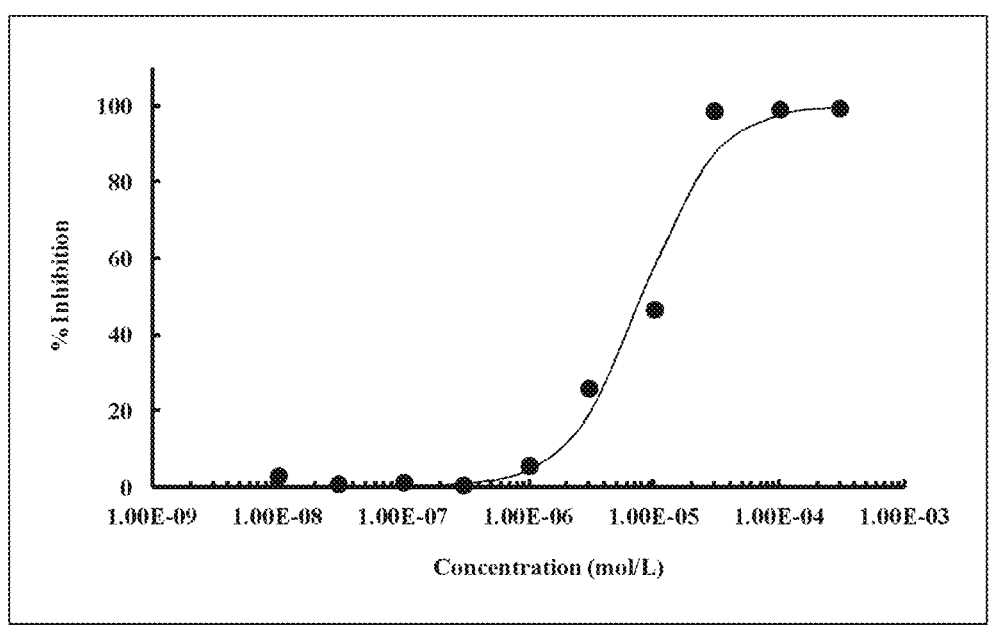
FIG. 4 is a graph for showing the results of assessment of PIK3CA/PIK3R1 inhibitory activity in Example 4.

The results are shown in FIG. 4. The $IC_{50}$ was 8.20 μM. As apparent from the results, CD-3 also showed kinase activity.

The invention claimed is:

1. A method of treating a disease that is treatable through inhibition of at least one kinase selected from the group consisting of CDK7, CDK4, CDK6, PIM2, TSSK3, MST4, NEK6, MAP3K, MST3, DDR1, SPHK1, CaMK1, AurA, BRK, CaMK4, and PIM1, the method comprising administering an effective dose of a compound represented by the following formula (1-1) or a salt thereof to a patient:

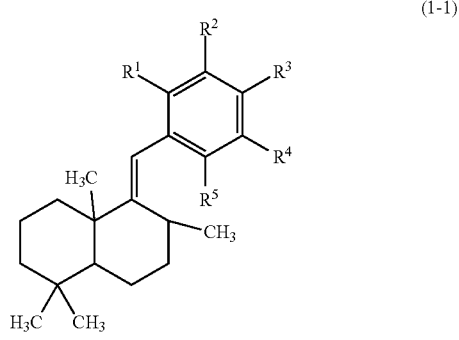

(1-1)

wherein $R^1$, $R^2$, $R^3$, $R^4$, and $R^5$ are identical to or different from each other, and each represent hydrogen, a hydroxy group, an acyl group, a hydroxyalkyl group, or a carboxyl group.

2. A method of treating a disease that is treatable through inhibition of PI3K and at least one additional kinase selected from the group consisting of CDK7, CDK4, CDK6, PIM2, TSSK3, MST4, NEK6, MAP3K, MST3, DDR1, SPHK1, CaMK1, AurA, BRK, CaMK4, and PIM1, the method comprising administering an effective dose of a compound represented by the following formula (1-1) or a salt thereof to a patient:

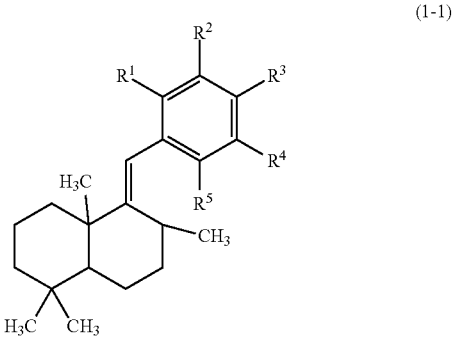

(1-1)

wherein $R^1$, $R^2$, $R^3$, $R^4$, and $R^5$ are identical to or different from each other, and each represent hydrogen, a hydroxy group, an acyl group, a hydroxyalkyl group, or a carboxyl group.

* * * * *